US009713510B2

(12) United States Patent
Aravena

(10) Patent No.: US 9,713,510 B2
(45) Date of Patent: Jul. 25, 2017

(54) DRILL LIMIT SYSTEM AND METHOD OF USING SAME

(71) Applicant: Implant Direct Sybron International LLC, Calabasas Hills, CA (US)

(72) Inventor: Ines Aravena, Santa Rosa Valley, CA (US)

(73) Assignee: Implant Direct Sybron International LLC, Thousand Oaks, CA (US)

( * ) Notice: Subject to any disclaimer, the term of this patent is extended or adjusted under 35 U.S.C. 154(b) by 168 days.

(21) Appl. No.: 14/660,408

(22) Filed: Mar. 17, 2015

(65) Prior Publication Data

US 2015/0257852 A1  Sep. 17, 2015

Related U.S. Application Data

(60) Provisional application No. 61/954,440, filed on Mar. 17, 2014, provisional application No. 62/130,905, filed on Mar. 10, 2015.

(51) Int. Cl.
*A61C 1/08* (2006.01)
*B23Q 16/00* (2006.01)
(Continued)

(52) U.S. Cl.
CPC .............. *A61C 1/082* (2013.01); *A61C 1/084* (2013.01); *B23Q 16/001* (2013.01);
(Continued)

(58) Field of Classification Search
CPC ......... A61C 1/082; A61C 1/084; A61C 1/145; A61C 1/186; B23Q 16/00; B23Q 16/001; B23Q 16/002; G01D 5/18
(Continued)

(56) References Cited

U.S. PATENT DOCUMENTS 1,495,887 A * 5/1924 Crane ................ B23Q 17/0938
                                                33/201
3,047,959 A * 8/1962 Selbert ............... B23Q 17/2225
                                                33/639
(Continued)

FOREIGN PATENT DOCUMENTS

DE      4323086 A1 *  1/1995 ........... B23Q 16/002
DE     10347313 A1 *  5/2005 ........... B23B 49/008
EP       556611 A1 *  1/1993 ............. B23Q 16/00

OTHER PUBLICATIONS

Ines Aravena, U.S. Appl. No. 62/130,927, filed Mar. 10, 2015 entitled Modular Surgical Tray.
(Continued)

*Primary Examiner* — R. A. Smith
(74) *Attorney, Agent, or Firm* — Wood Herron & Evans LLP

(57) ABSTRACT

A drill limit system includes a holder having drill stops removably coupled thereto and configured to receive a drill bit therethrough, and a platform coupled to the holder and configured to engage a tip end of the drill bits when received through the drill stops, wherein the holder and platform are movable relative to each other so that the position of the drill stops relative to the drill bits may be selectively varied. A method for attaching drill stops to a drill bit includes providing a holder and a platform movable relative to each other, the holder having a plurality of drill stops removably coupled thereto, inserting a plurality of drill bits through respective drill stops, moving the holder and platform relative to each other to select a desired height of the drill stops on the bits, and engaging the drill stops to the drill bits at the selected height.

20 Claims, 23 Drawing Sheets

(51) Int. Cl.
  *A61C 8/00*   (2006.01)
  *A61C 1/18*   (2006.01)
  *A61B 90/00*  (2016.01)

(52) U.S. Cl.
  CPC ......... *A61B 2090/033* (2016.02); *A61C 1/186* (2013.01); *A61C 8/0089* (2013.01); *Y10T 29/49826* (2015.01)

(58) Field of Classification Search
  USPC ......... 33/201, 636, 637, 638, 639, 640, 642; 206/379; 211/69; 408/16, 202, 203, 408/241 R, 241 S; 433/75, 79, 165; 606/172
  See application file for complete search history.

(56) References Cited

U.S. PATENT DOCUMENTS

| | | |
|---|---|---|
| 3,270,416 A | 9/1966 | Massa |
| 6,514,258 B1 | 2/2003 | Brown et al. |
| 6,726,414 B2 * | 4/2004 | Pientka et al. ....... B23Q 16/024 144/136.95 |
| 6,739,872 B1 | 5/2004 | Turri |
| 7,048,477 B2 * | 5/2006 | Abrams ............. A61B 17/1617 408/1 R |
| 7,695,279 B2 | 4/2010 | Hirsch et al. |
| 9,414,894 B1 * | 8/2016 | Mansueto ................ A61C 3/04 |
| 2007/0099150 A1 | 5/2007 | Muller et al. |

OTHER PUBLICATIONS

International Application No. PCT/US15/20969 filed Mar. 17, 2015 entitled Drill Limit System and Method of Using Same.
Ines Aravena, U.S. Appl. No. 29/520,045, filed Mar. 10, 2015 entitled Modular Surgical Tray and Portions Thereof.
International Searching Authority, International Search Report and Written Opinion issued in International Application No. PCT/US2015/020969 dated Jun. 22, 2015.

\* cited by examiner

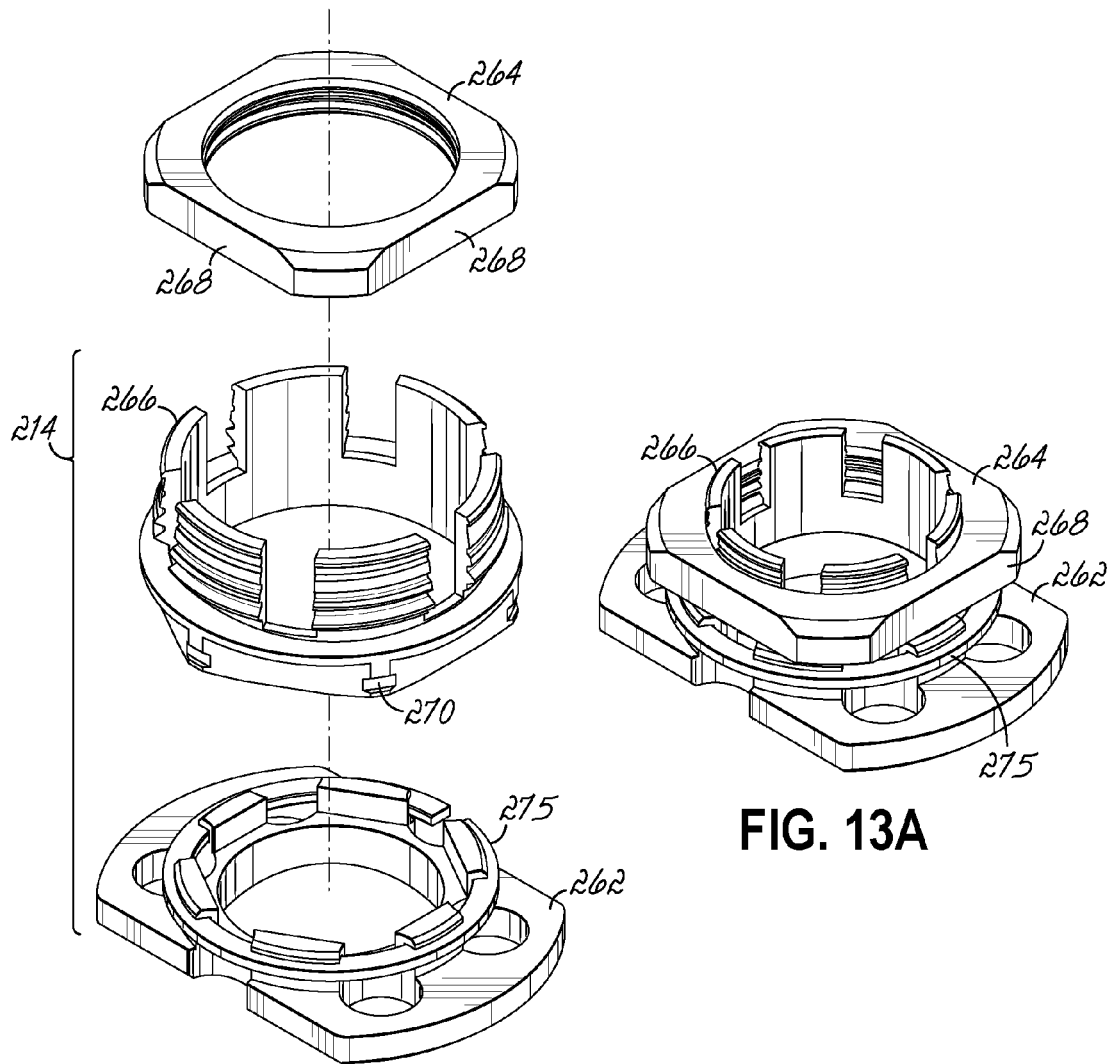
FIG. 13
FIG. 13A
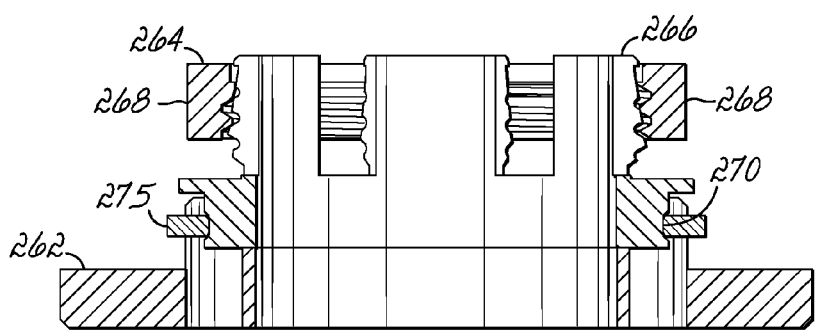
FIG. 13B

DRILL LIMIT SYSTEM AND METHOD OF USING SAME

CROSS REFERENCE TO RELATED CASES

This application claims the benefit of U.S. Provisional Patent Application Ser. No. 61/954,440 filed Mar. 17, 2014, and U.S. Provisional Patent Application Ser. No. 62/130,905 filed Mar. 10, 2015, the disclosures of both of which are incorporated by reference herein in their entirety.

TECHNICAL FIELD

The present invention relates generally to a drill limit system and, more particularly, to a drill limit system for drilling a bone with a dental drill during a medical procedure, such as a dental implantation.

BACKGROUND

Drilling a bone with a drill tends to generate heat within the bone that may harm the bone or other surrounding living tissues of a patient. Unfortunately, increased heat often results in an increased risk of harm to the patient. For this reason, a practitioner, such as a dentist, nurse, or other medical professional, traditionally drills the hole so as to reduce the amount of heat generated within the bone. To do so, the practitioner initially uses a relatively small drill bit for drilling a similarly small hole in the bone to a desired depth. The practitioner then uses a relatively larger drill bit for drilling a relatively larger hole coaxially through the smaller hole to the same desired depth. The practitioner may then repeat enlarging the hole with additional, larger drill bits until the hole has a desirable diameter and depth. By enlarging the hole incrementally with progressively larger drill bits, the practitioner is able to more efficiently and effectively remove a portion of the bone to form the hole with less heat than drilling immediately with a drill bit having the desired diameter.

While drilling the hole repeatedly, such as during a dental procedure, controlling the drilling depth is crucial to a successful outcome for the patient. On one hand, drilling the hole too deep may damage tissue, nerves, and/or perforate the sinus cavity of the patient. On the other hand, drilling the hole too shallow may not provide enough foundation in which to secure a dental implant. To increase the likelihood of repeatedly drilling the hole to the desired depth, the practitioner often uses a drill bit having a visual marker and/or a drill stop for indicating a desired drilling depth during the procedure. A drill bit including a visual marker for depth may accurately indicate depth, but fails to provide a physical stop to inhibit the practitioner from drilling too deep. Also, known drill stops are typically small in size for fitment between teeth and may be easily lost or misplaced before, during, or after the dental procedure. In any case, these marked drill bits and drill stops often come in sets for drilling a variety of hole sizes, and as such, are expensive to purchase and difficult to handle during the busy atmosphere of the dental procedure.

Therefore, there is a need for a drill limit system and method for drilling a bone, such as a tooth and/or jawbone, that addresses present challenges and characteristics discussed above.

SUMMARY OF INVENTION

To these ends, a drill limit system for providing a plurality of drill stops with drill bits includes a holder and a platform. The holder includes a plurality of drill stops removably coupled to the holder and configured to receive a drill bit therethrough. The drill stops have a first state in which the drill bits are configured to be movable relative to the drill stops and a second state in which the drill stops are configured to be fixedly secured to the drill bits. The platform includes a surface configured to engage a tip end of the drill bits. The holder and the platform are movable relative to each other such that the position of the drill stops relative to the drill bits may be selectively varied in order to locate the drill stops at a desired position on the drill bits.

In one embodiment, the platform is stationary and the holder is configured to be movable relative to the platform. In an alternative embodiment, however, the holder is stationary and the platform is configured to be movable relative to the holder. In this embodiment, the drill limit system may include a rotatable adjustment member such that rotation of the adjustment member causes movement of the platform relative to the holder. More particularly, the adjustment member may include a glide element configured to move along a helical groove on the platform such that rotation of the adjustment member causes the platform to move relative to the holder.

The drill stops are configured to be removably coupled to the holder. In one embodiment, the holder includes one or more spring clips for selectively engaging the drill stops to and releasing the drill stops from the holder. In this regard, with a sufficient force, the spring clips may flex so as to release the drill stop from the holder. The spring clips may also be configured to all the drill stops to snap back into engagement with the holder. The spring clips may include one or more spring fingers or C-springs. The drill stops may include a clip feature configured to cooperate with the spring clips.

In one embodiment, the drill stops include a nut portion and a grip portion threadably coupled to the nut portion. With such an arrangement, rotation of the nut portion relative to the grip portion transitions the drill stops between the first and second states. The grip portion may include a clip feature configured to cooperate with one or more spring clips on the holder for selectively engaging the drill stops to and releasing the drill stops from the holder. The holder may include a rotatable member configured to rotate the nut portion relative to the grip portion when the rotatable member is turned. The drill limit system may include a torque-control tool configured to engage the nut portion of the drill stop or the rotatable member so as to secure the drill stops to the drill bits.

In another embodiment, a method for attaching drill stops to a drill bit includes providing a holder and a platform movable relative to each other, the holder including a plurality of drill stops removably coupled to the holder, inserting a plurality of drill bits through respective drill stops in the holder so that a portion of the drill bits engage the platform, moving the holder and platform relative to each other to select a desired height of the drill stops on each of the drill bits, and engaging a drill stop onto each of the plurality of drill bits at the selected height. In one embodiment, the platform is held stationary and the holder is moved relative to the platform. In an alternative embodiment, however, the holder is held stationary and the platform is moved relative to the holder.

The method for attaching drill stops to a drill bit additionally includes rotating a first portion of the drill stop relative to a second portion of the drill stop to engage the drill stop onto each of the plurality of drill bits. Rotating the first portion of the drill stop relative to the second portion of the drill stop may be accomplished by rotating a rotatable member of the holder that is in contact with the first portion of the drill stop

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain various aspects of the invention.

FIG. 13 is a schematic view of a portion of an alternative embodiment of the drill bit assembly.

FIG. 13A is a schematic view of the portion of an alternative embodiment of the drill bit assembly, as shown in FIG. 13.

FIG. 13B is a schematic cross-sectional view of the view shown in FIG. 13A.

DETAILED DESCRIPTION

Figure 1:
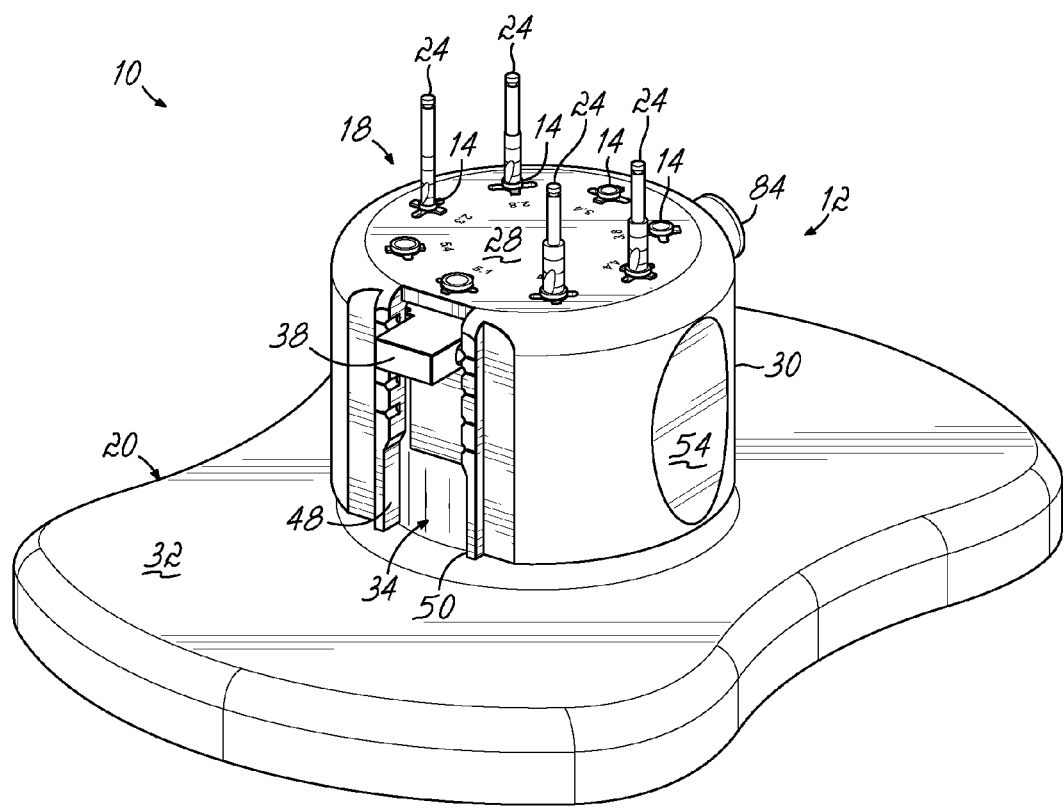
FIG. 1 is a top perspective view of a drill platform of drill limit system according to an embodiment of the invention including a plurality of drills.

Although the invention will be described next in connection with certain embodiments, the invention is not limited to practice in any one specific type of drill limit system. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described herein could be arranged in multiple different ways.

With reference to FIGS. 1-4C, a drill limit system 10 for drilling a bone, such as a tooth and/or jawbone, during a medical procedure, such as an osteotomy or other endodontic and dental surgeries, includes a drill platform 12 having a plurality of drill stops 14 and a torque-control tool 16. The drill stops 14 are removably connected to a holder 18 offset from a pedestal 20 for receiving a plurality of drill bits 24 (see FIG. 6B). A practitioner, such as a doctor, nurse, or other medical professional, moves the holder 18 relative to the pedestal 20 to set a desirable depth for drilling a tooth and/or jawbone with the plurality of drill bits 24, and then positions each of the drill bits 24 within a corresponding drill stop 14. Alternatively, the drill bits may be positioned in a corresponding drill stop 14 and then the holder 18 moved relative to the pedestal 20 to set a desired depth. The torque-control tool 16 may then be used to tighten each drill stop 14 to each respective drill bit 24 such that the practitioner may remove and replace each drill bit 24 with the connected drill stop 14 during the medical procedure. At the conclusion of the medical procedure, the torque-control tool 16 may be used to loosen each of the drill stops 14 from the respective drill bits 24 so that the practitioner may remove the drill bits 24 from the drill platform 12. As such, the drill limit system 10 may be cleaned, maintained, or otherwise handled by the practitioner while the drill stops 14 remain on either the holder 18 or one of the respective drill bits 24 during use. According to an exemplary embodiment, the drill limit system 10 includes eight drill stops 14 arranged proximate to an outer perimeter of the holder 18 for receiving eight respective drill bits 24 of a variety of diameters. It will be appreciated that the holder 18 may be configured to hold any number of drill stops 14 for drill bits 24 of any desirable diameter. In this respect, the invention is not intended to be limited to accommodating any particular set of drill bits 24.

Figure 6A:
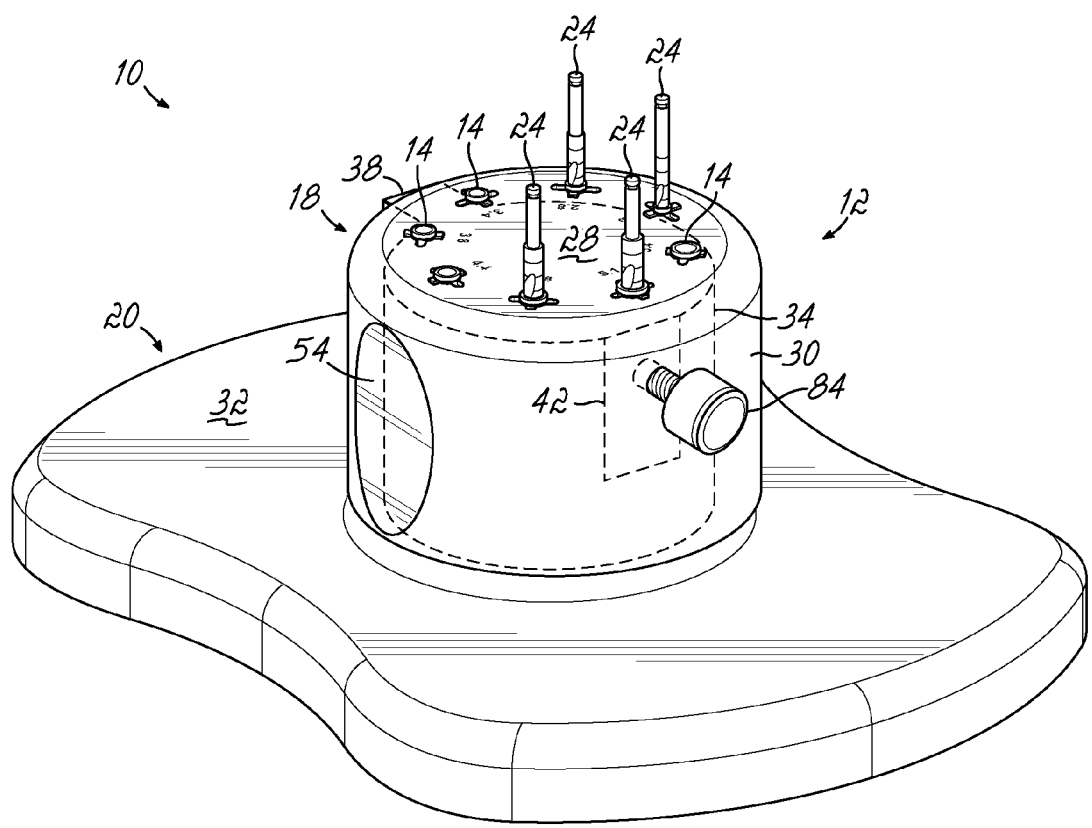
FIG. 6A is a right perspective view of the drill platform shown in FIG. 1.
Figure 6B:
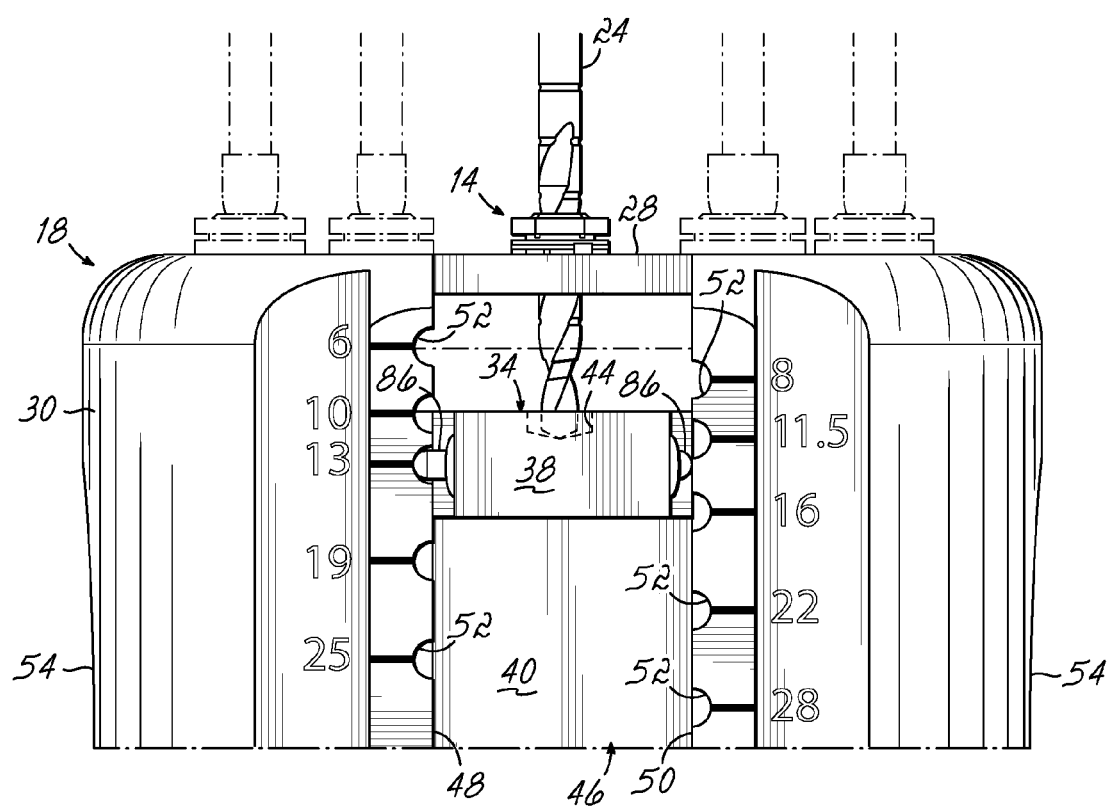
FIG. 6B is a front view of the drill platform shown in FIG. 1.

As briefly discussed above, the drill platform 12 includes the holder 18 for holding the plurality of drill stops 14 and the pedestal 20, wherein the holder 18 and pedestal are movable relative to each other for setting a variable depth therebetween (see FIG. 6B). According to an exemplary embodiment, the holder 18 is generally cup-shaped and has a generally planar endwall 28 and an annular sidewall 30 projecting downward from the planar endwall 28 toward a base 32 of the pedestal 20 when the drill platform is assembled. The pedestal 20 further includes a shaft 34 projecting upward from the base 32. The shaft 34 is configured for slidably receiving the holder 18 such that the holder 18 is generally free to move upward or downward on or relative to the shaft 34. As shown in FIGS. 1-4C, the base 32 is generally planar and configured for resting on a relatively flat surface, such as a table, countertop, tray, etc. during the medical procedure for easy access by the practitioner.

The terms "upward" and "downward" are descriptive terms of one embodiment of the relative vertical positions of, for example, the base 32 to the holder 18. In this respect, the terms "upward" and "downward" are merely exemplary and not intended to limit the invention described herein. For example, the drill limit system 10 according to another exemplary embodiment may be reconfigured for an alternative placement proximate to the practitioner at a generally horizontal or other angled arrangement. Thus, these terms should not limit the present invention to a particular orientation.

Figure 4A:
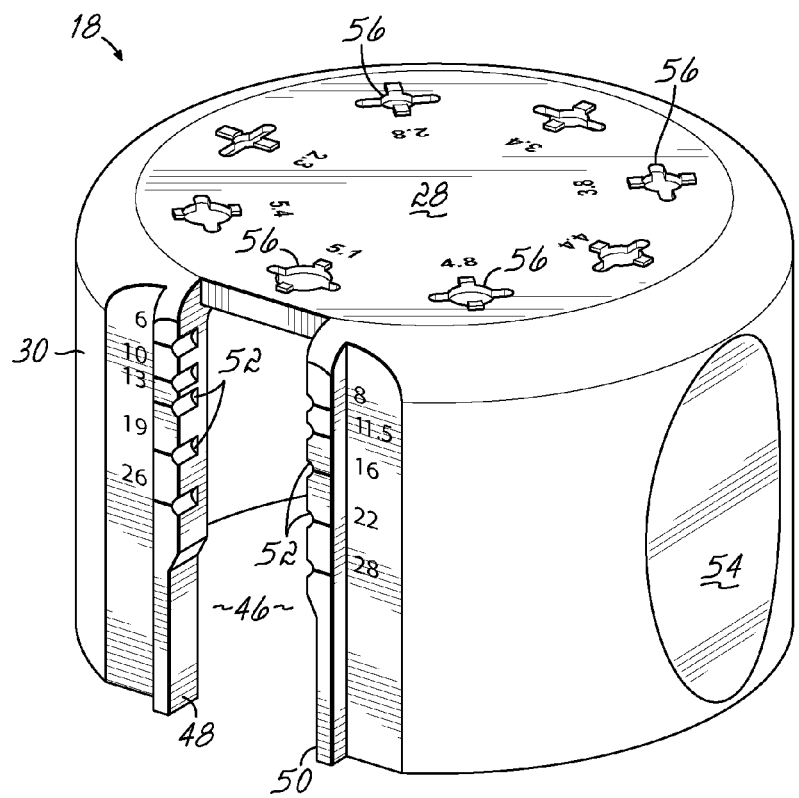
FIG. 4A is a front perspective view of a holder of the drill platform shown in FIG. 3.
Figure 4B:
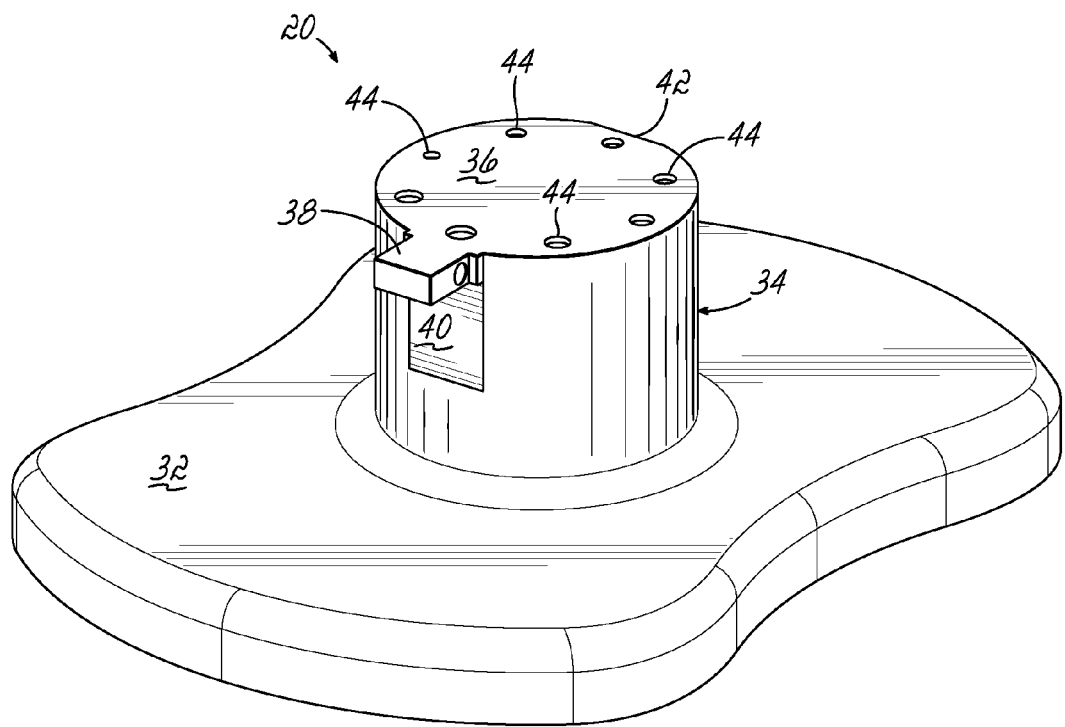
FIG. 4B is a front perspective view of a base of the drill platform shown in FIG. 3.

With respect to FIGS. 1 and 4A-4B, the shaft 34 is generally cylindrical and further includes a top surface 36, a depth lock 38 projecting from a side 40 of the shaft 34, and a flat surface 42 on the side opposite the depth lock 38. The depth lock 38 and the flat surface 42 are both configured for cooperating with the holder 18 for setting and maintaining the position of the drill stops 14 relative to the drill bits 24, as will be discussed below in greater detail. The top surface 36 is generally horizontal and includes a plurality of recesses 44 configured to receive the drill bits 24 at a uniform vertical position relative to the holder 18. In this respect, each recess 44 generally vertically aligns with a respective drill stop 14, such that each drill bit 24 is held within the holder 18 in a generally vertical orientation and the tips of the drill bits 24 are positioned in the recesses 44.

The holder 18 includes a generally vertical slot 46 extending through the annular sidewall 30 defining a pair of opposing inner end walls 48, 50. The slot 46 is sized to receive the depth lock 38 such that the inner end walls 48, 50 are vertically movable relative to the depth lock 38. More particularly, the inner end walls 48, 50 each include a plurality of depth detents 52 positioned vertically therealong in predetermined positions for positioning the drill stop 14 relative to the drill bit 24. Each depth detent 52 is configured to engage the depth lock 38 such that the practitioner may feel, hear, and/or visualize the setting for enhanced feedback. To further aid the practitioner in manipulating the holder 18, the holder 18 includes one or more grip surfaces 54 positioned about the annular sidewall 30.

Figure 2:
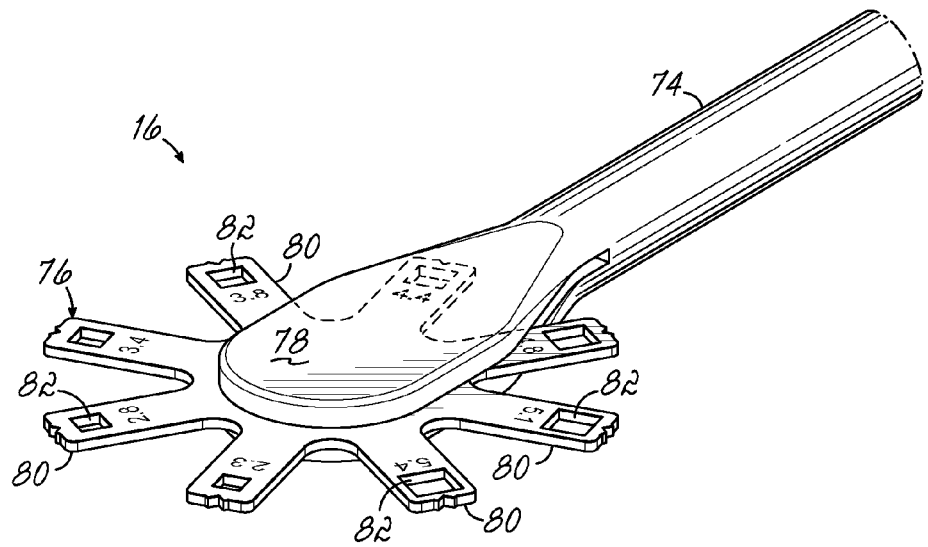
FIG. 2 is a top perspective view of a torque-control tool of the drill limit system shown in FIG. 1.
Figure 3:
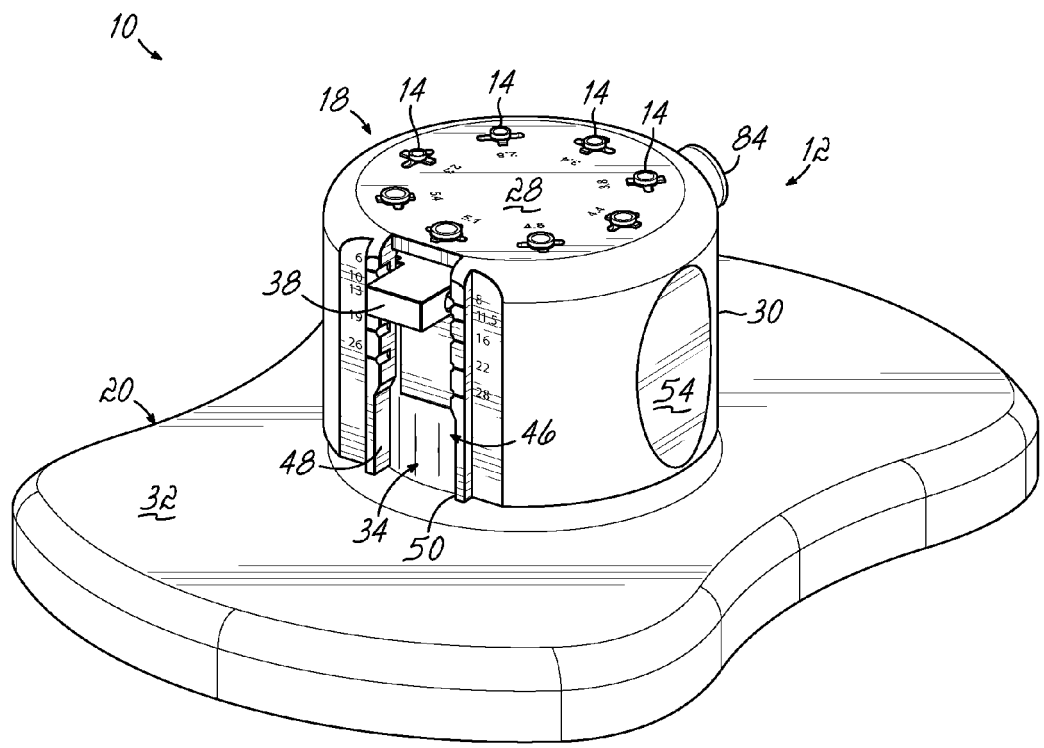
FIG. 3 is a front perspective view of the drill platform shown in FIG. 1.
Figure 4C:
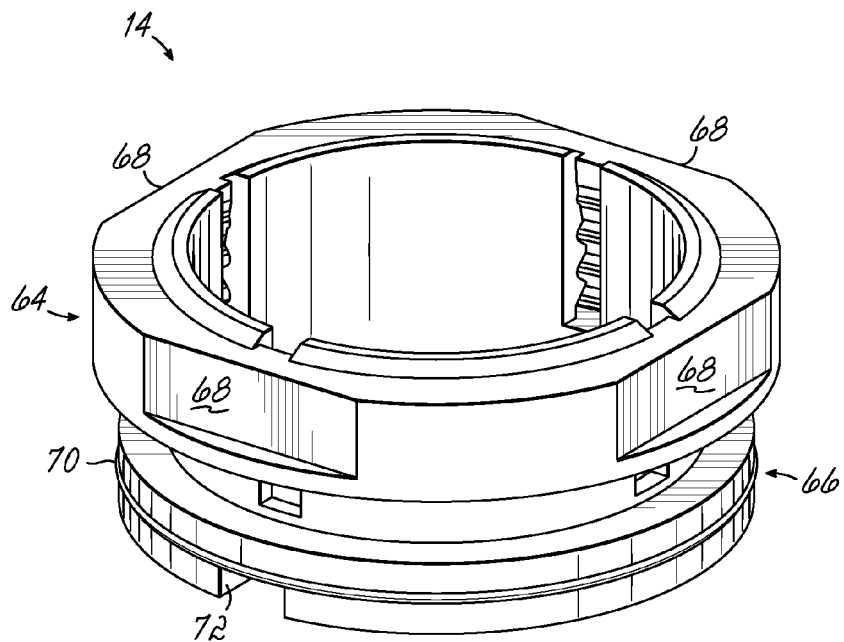
FIG. 4C is a front perspective view of a drill stop shown in FIG. 3.

FIG. 4C shows an exemplary drill stop 14 configured to cooperate with the holder 18, the drill bits 24, and the torque-control tool 16 of FIGS. 1-2. The drill stop 14 includes a nut portion 64 configured for being received by the torque-control tool 16 and a grip portion 66 configured for gripping to a drill bit 24. The nut portion 64, such as a lock nut having internal threads and a plurality of external flats 68, is operatively connected to and rotatable relative to the grip portion 66, and more particularly externally threaded split fingers, such that rotating the nut portion 64 in a first direction relative to the grip portion 66 causes the grip portion 66 to reduce in diameter and tighten onto the drill bit 24. This is accomplished by essentially clamping the resilient split fingers of the grip portion 66 onto the drill bit 24. The grip portion 66 also includes a clip feature 70 for removably securing the drill stop 14 to the holder 18, as discussed below. In an exemplary embodiment, the clip feature 70 may be configured as an annular ring protruding outward from the grip portion 66. In addition, the grip portion 66 includes a pair of opposing grooves 72 in a bottom surface of the grip portion 66, the purpose of which will be described below.

Figure 5:
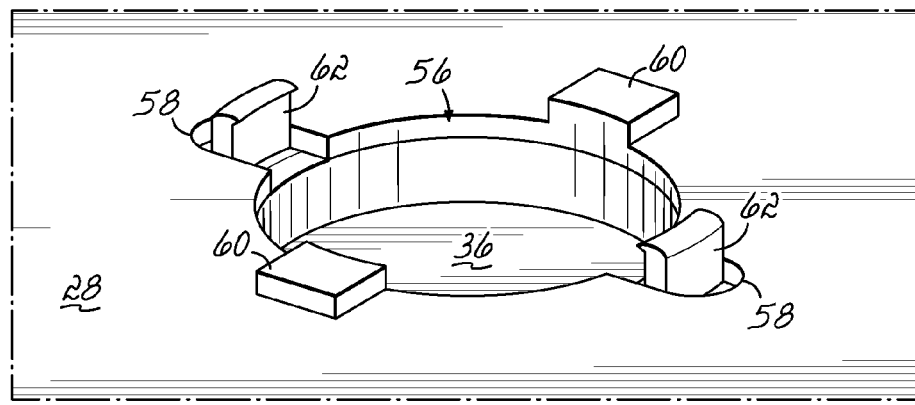
FIG. 5 is an enlarged perspective view of the drill platform shown in FIG. 3 having a pair of flexing elements.

As discussed briefly above and with respect to FIGS. 4A-5, the planar endwall 28 of holder 18 includes a plurality of holes 56 for receiving the drill stops 14 and, in turn, the drill bits 24 (see FIG. 1). According to an exemplary embodiment, holes 56 extend vertically through the planar endwall 28 toward the top surface 36 of the shaft 34 proximate to the outer perimeter of the holder 18. For each of the holes 56, the planar endwall 28 further includes a pair of opposing recesses 58 extending into the hole 56 and a pair of opposing abutments 60 projecting upward from the planar endwall 28 adjacent to the hole 56 (see FIG. 5). More particularly, the abutments 60 and recesses 58 may be approximately 90 degrees offset from each other. Each recess 58 includes an L- or J-shaped spring clip 62 extending from the planar endwall 28, such as via a separate element mounted on an underside surface of endwall 28 or integrally formed with endwall 28, adjacent to the hole 56. The spring clip 62 is configured to removably engage the drill stop 14 concentrically about the hole 56 via clip feature 70 of grip portion 66. While an exemplary embodiment includes spring clips 62 for removably connecting the drill stops 14 to the planar endwall 28, it will be appreciated that another structure for removably connecting the drill stop 14 to the planar endwall 28 about the hole 56 may be similarly used. Once the drill stop 14 is positioned relative to the hole 56, each abutment 60 cooperatively engages the opposing grooves 72 of drill stop 14 to inhibit rotation of the grip portion 66 while the nut portion 64 rotates, thereby tightening (or loosening) the drill stops 14 to the drill bits 24.

In accordance with the invention, the practitioner manipulates the torque-control tool 16 in order to tighten and/or loosen the drill stop 14 relative to the drill bit 24. The torque-control tool 16 includes a handle 74 for the practitioner to grip and a rotatably connected socket wheel 76. The handle 74 extends to a detent end 78, which receives the socket wheel 76 similar to that of a pinwheel. The socket wheel 76 includes a plurality of radial projections 80, or spokes, projecting outward from a central portion of the socket wheel 76. Each radial projection 80 includes a socket hole 82 sized to receive the flats 68 of the nut portion 64 discussed above. According to an exemplary embodiment, the socket wheel 76 includes eight projections 80 with socket holes 82 sized to correspond to the eight drill bits 24 discussed above. However, it will be appreciated that the number of the projections 80 may vary in accordance with the number of drill bits 24 and drill stops 14 to be used with the system 10.

To select the desired projection 80 for the desired drill stop 14, the practitioner rotates the socket wheel 76 such that the projection 80 is axially aligned with and projecting away from the handle 74. In addition, the socket wheel 76 includes a torque limit mechanism in which the socket wheel 76 is biased, such as with a spring (not shown) within the detent end 78 to hold the socket wheel 76 in such an aligned position up to a desired amount of torque. For example, the practitioner may tighten the nut portion 64 of the drill stop 14 until the desired amount of torque is reached, at which point the socket wheel 76 ratchets free of the biased alignment to indicate to the practitioner that the nut portion 64 is sufficiently tightened. According to an exemplary embodiment, an exemplary desired amount of torque may be approximately 60 Ncm. Of course, this torque value may vary depending on the particular application. As such, the biased ratcheting of the socket wheel 76 further inhibits the practitioner from over tightening, which may damage the drill stop 14, and from under tightening, which may result in the drill stop 14 coming loose during use.

In use, FIGS. 6A-6B show the drill platform 12 having the drill bits 24 resting loosely within the drill stops 14. The practitioner loosens a locking element 84 from against the flat surface 42 of the side of the shaft 34. The locking element 84, such as a set screw, threadably engages the annular sidewall 30 of the holder 18 and remains in the holder 18 once the locking element 84 is loosened. With the locking element 84 loosened, the holder 18 is movable vertically upward and downward relative to the top surface 36 of the shaft 34 to define the variable depth therebetween, i.e. between endwall 28 and top surface 36 of shaft 34. As shown in FIG. 6B, an exemplary embodiment of the depth lock 38 includes a pair of opposing biased pins 86 that engage the predetermined depth detents 52 for setting the variable depth. A plurality of numerals positioned adjacent to each depth detent 52 indicate a corresponding depth to which the drill bits 24 will be removably connected to the drill stops 14. When a desirable depth is selected, the practitioner tightens the locking element 84 against the shaft 34 to lock the holder 18 relative to the shaft 34.

Figure 7A:
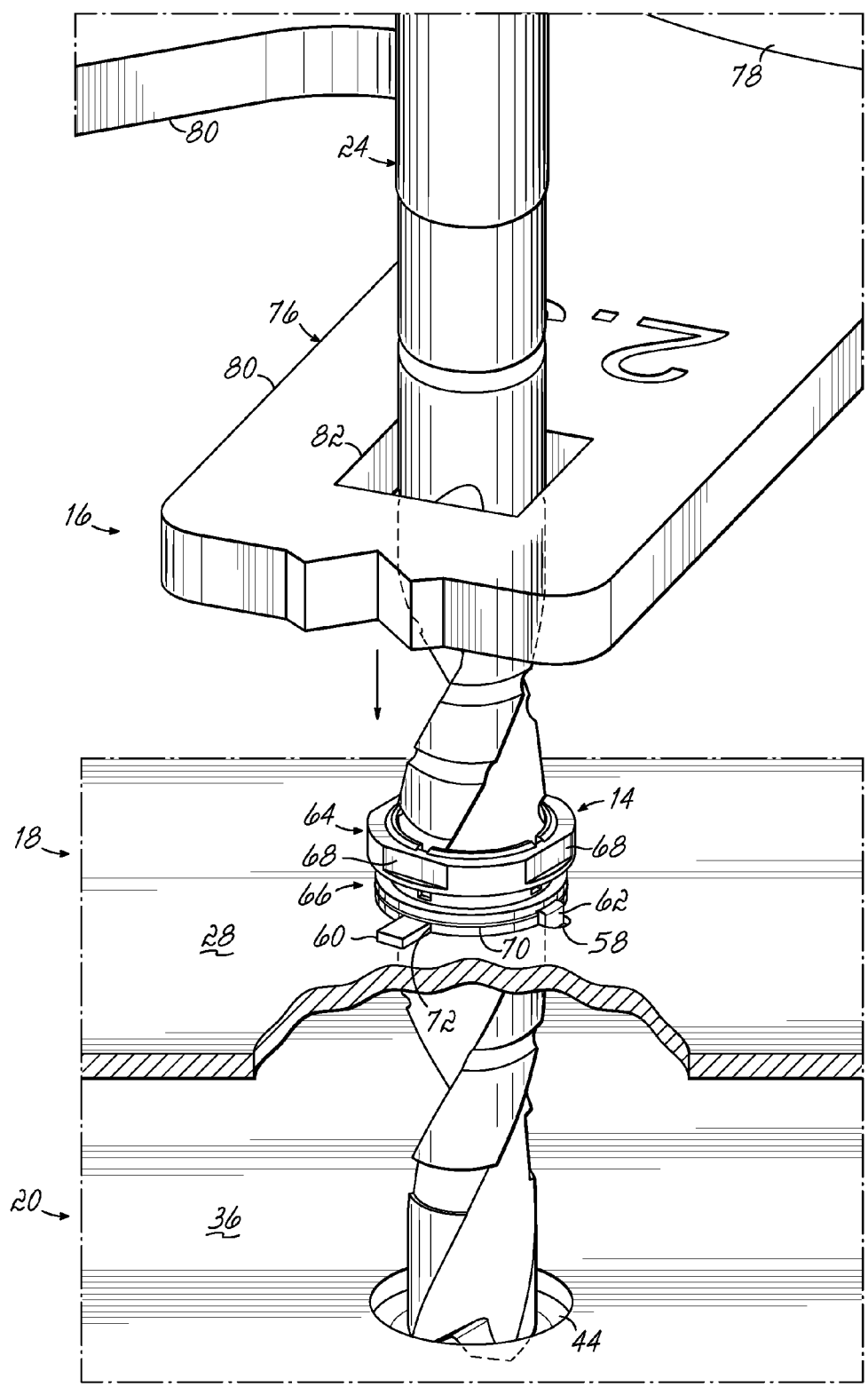
FIG. 7A is an enlarged perspective view of the torque-control tool, a drill stop, a drill and the drill platform shown in FIG. 1.
Figure 7B:
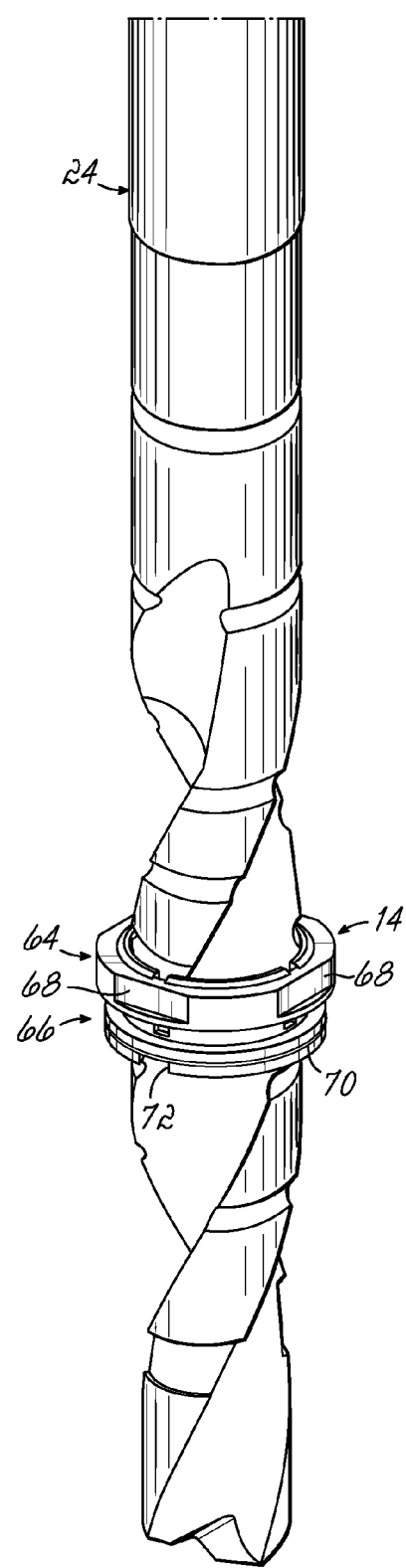
FIG. 7B is an enlarged perspective view of the drill stop tightened to the drill as shown in FIG. 7A.

With respect to FIGS. 7A-7B, the practitioner selects the corresponding projection 80 of the socket wheel 76 and slides the socket hole 82 onto the drill bit 24 until the socket hole 82 engages the flats 68 of the nut portion 64. The practitioner manipulates the handle 74 to rotate the nut portion 64 relative to the grip portion 66 to clamp the grip portion 66 onto the drill bit 24. Once the drill stop 14 is connected to the drill bit 24, the socket wheel 76 ratchets free to indicate that an appropriate amount of torque has been applied to the drill stop 14. The practitioner repeats this tightening for each of the drill stops 14 and corresponding drill bits 24 in the drill platform 12.

From the smallest diameter drill to the largest diameter drill necessary to drill a desirable hole in the bone, the practitioner forms the hole by disengaging the drill bit 24 from the holder 18. To disengage the drill bit 24 from the holder 18, the practitioner pulls the drill bit 24 generally upwardly with sufficient force to overcome the hold of the spring clip 62 to the clip feature 70 of grip portion 66. The practitioner then drills a hole in the bone with the drill bit 24 to the desired depth, as indicated by the drill stop 14, and then replaces the drill stop 14 and drill bit 24 back into its corresponding hole 56 and reengaging the spring clip 62 and spring feature 70. The practitioner repeats this disengaging, drilling, and replacing of the drill stops 14 and drill bits 24 until the hole in the bone is at the desirable diameter and at the desired depth as determined by the drill stops 14.

Once the hole in the bone is complete, the practitioner loosens each of the drill stops 14 from the drill bits 24 as discussed above, and removes the drill bits 24 from the drill platform 12. The locking element 84 is then loosened from the shaft 34, and the holder 18, including the drill stops 14, is removed from the shaft 34 for cleaning and other routine maintenance in order to prepare the drill limit system 10 for another medical procedure.

Figure 8:
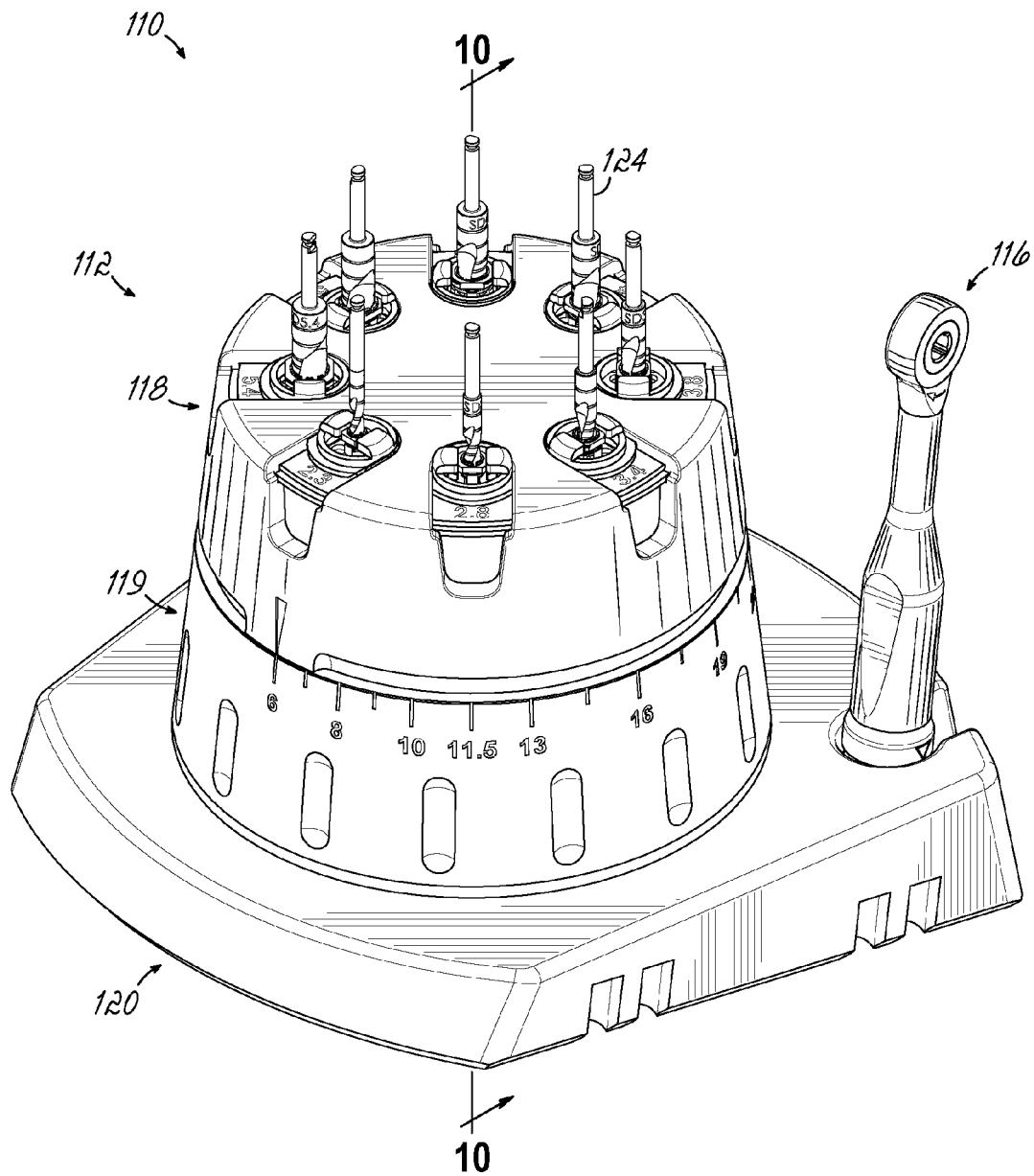
FIG. 8 is a top perspective view of a drill limit system according to an embodiment of the invention including a plurality of drills.
Figure 9:
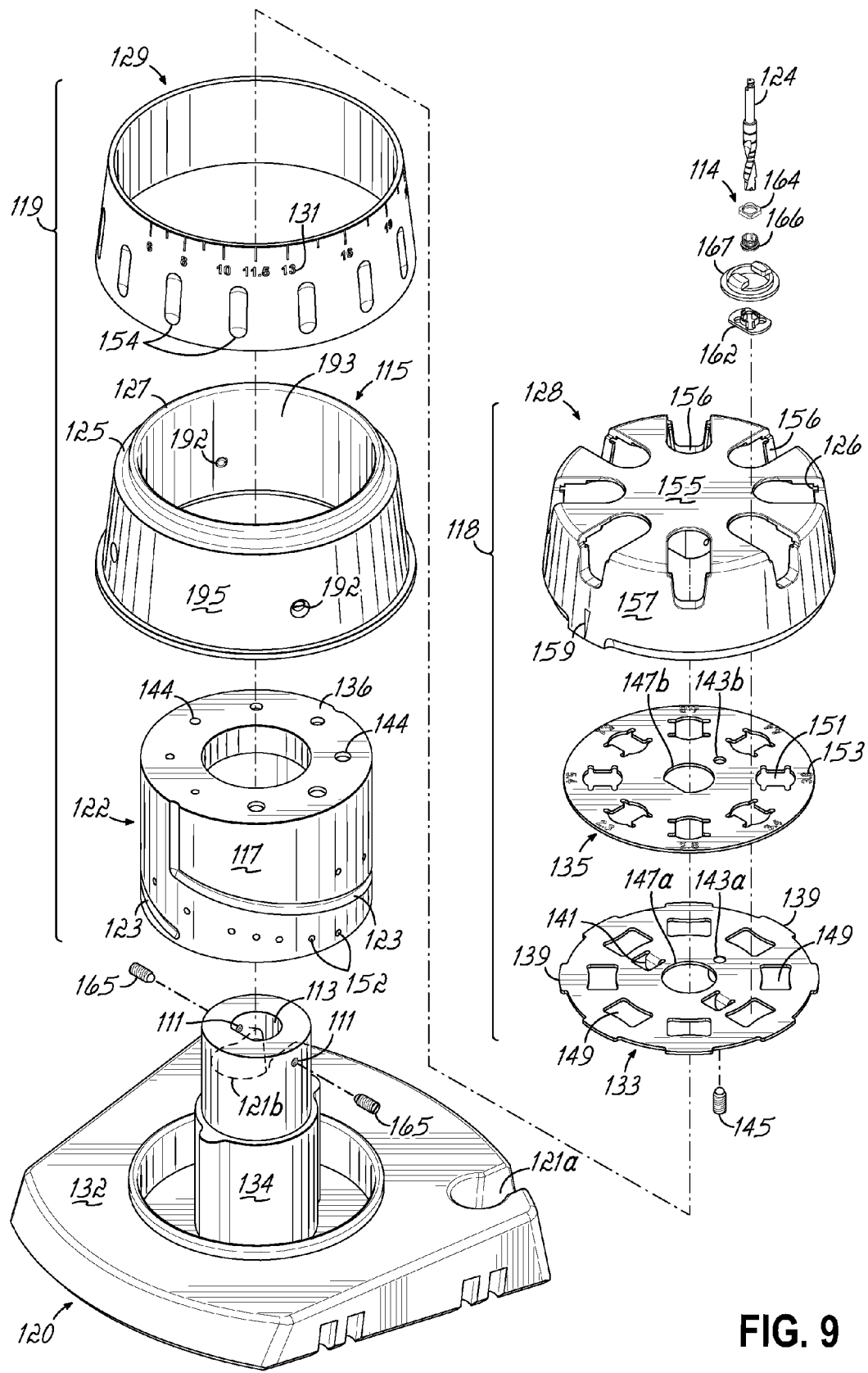
FIG. 9 is a schematic representation of the drill limit system as shown in FIG. 8.

FIGS. 8-18 show alternative embodiments of the drill limit system, where like labels indicate similar components. As best shown in FIGS. 8 and 9, drill limit system 110 includes a drill platform 112 and a torque-control tool 116. The drill platform 112 includes holder portion 118, depth control portion 119, and pedestal 120.

Pedestal 120 is composed of base 132 and shaft 134. Base 132 contains specially adapted recesses 121a and 121b for receiving the torque-control tool 116 and is generally planar and configured for resting on a relatively flat surface, such as a table, countertop, tray, etc. during the medical procedure for easy access by the practitioner. Shaft 134 is generally cylindrical, projecting away from the base 132, and is configured for slidably receiving the depth control portion 119 such that the depth control portion 119 is generally free to move in a certain direction on the shaft 134, which is shown as a vertical direction in the figures. The shaft 134 contains an upper portion that projects beyond the depth control portion 119 and interacts with holder portion 118 through threaded through-hole 111 and bore 113, which are described in greater detail below.

Depth control portion 119 is composed of variable depth platform 122, which fits over shaft 134, depth control member 115, and indicator ring 129. Variable depth platform 122 is composed of top surface 136, having a plurality of recesses 144 configured to receive the tip of drill bits 124, and an annular sidewall 117, which contains helical grooves 123 and depth notches 152. Depth control member 115, which is configured to interact with variable depth platform 122 in a manner discussed more fully below, is composed of a top surface 125 with a raised joining ring member 127 and an annular sidewall 195. Raised joining ring member 127 is configured to interact with cap 128 of the holder portion 118. The indicator ring 129 fits over the depth control member 115 and contains a plurality of grip features 154 to aid the practitioner in turning the depth control member 115, as well as a plurality of indicia of depth 131.

Holder portion 118 is composed of bottom plate 133, upper plate 135, flexing element 162, rotatable socket drive adapter 167, and cap 128. The drill bits 124 and drill stops 114 rest within holder portion 118 when not in use during the medical procedure. Bottom plate 133 and upper plate 135 possess an annular geometry of substantially equal diameter. However, bottom plate 133 includes a plurality of guide protrusions 139 configured to fit within openings 156 of cap 128 and to rest in ridges 126 of cap 128. Bottom plate 133 also contains one or more tabs 141, which can be used for inserting bottom plate 133 into the ridges 126, as well as one or more threaded holes 143a configured to align bottom plate 133 with upper plate 135 and cap 128. Bottom plate 133 has a center hole 147a and a plurality of openings 149 at least as large as the diameter of the drill bit 124. Upper plate 135 also includes one or more holes 143b configured to align upper plate 135 to bottom plate 133 and cap 128, as well as center hole 147b. The cap 128, upper plate 135, and bottom plate 133, are held in contact with ball bearing set screw 145. Flexing element 162 is configured to fit within a plurality of flexing element alignment openings 151 of upper plate 135, which generally align with openings 149 of the bottom plate 133. The number of bottom plate openings 149 and upper plate flexing element alignment openings 151 is determined by the number of drill bits 124 and drill stops 114 desired. In the figures, eight drill bits 124 and drill stops 114 are shown, but the invention is not so limited. The rotatable socket drive adapter 167 has an annular base 169, with a diameter greater than the corresponding opening 156 in cap 128, and wings 171. The rotatable socket drive adapter 167, which rests on upper plate 135, is placed over flexing element 162.

Conveniently, one or both of the flexing element 162 and the rotatable socket drive adapter 167 may be color coded to quickly indicate to the practitioner the matching sets of components. Additionally, a plurality of indicia 153 may be printed, etched, or otherwise included, proximate to the flexing element alignment openings 151 of upper plate 135 to indicate to the practitioner the diameter of the drill bit 124 housed at each flexing element alignment opening 151.

Figure 9A:
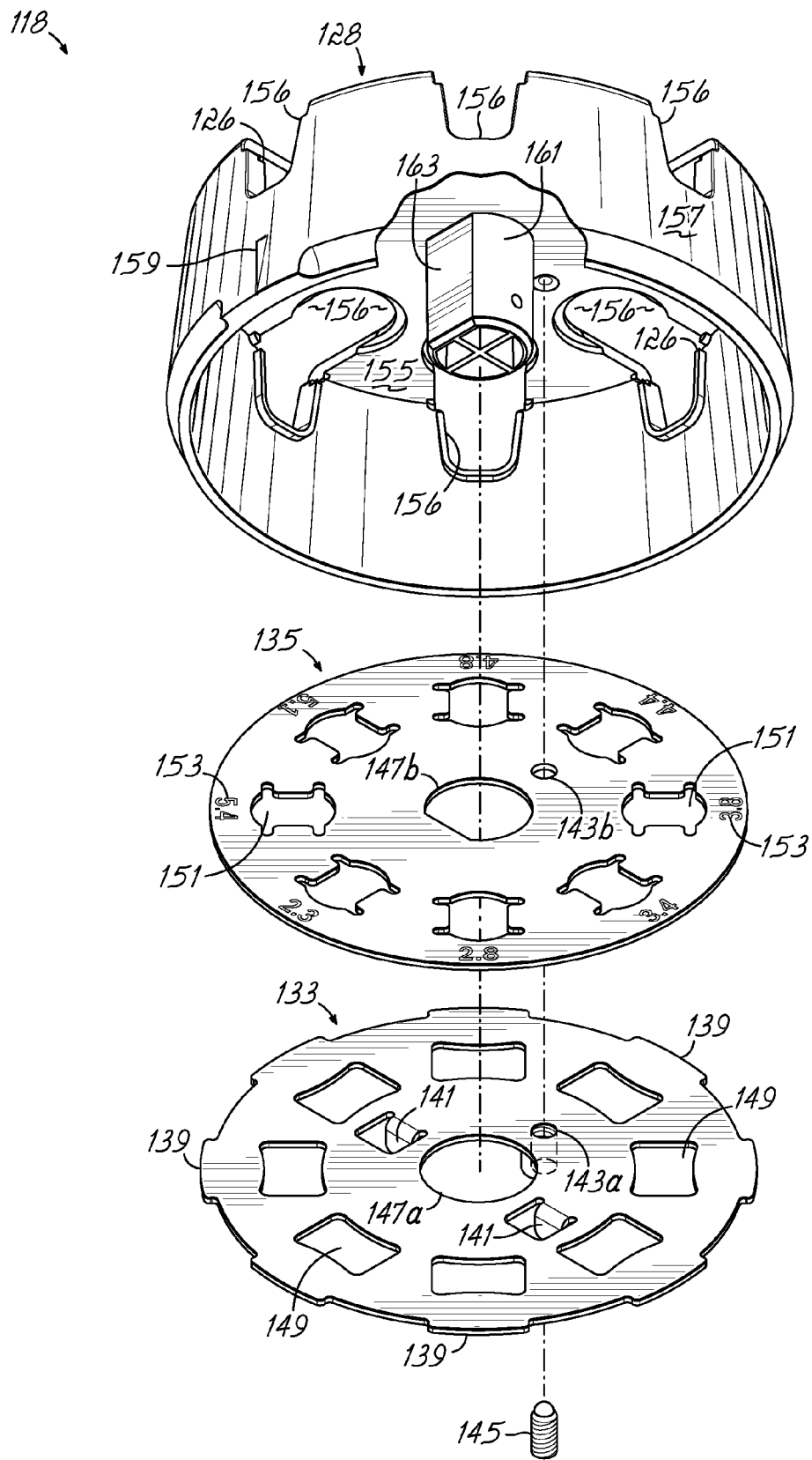
FIG. 9A is a schematic view of the cap 128 as shown in FIG. 9.
Figure 9B:
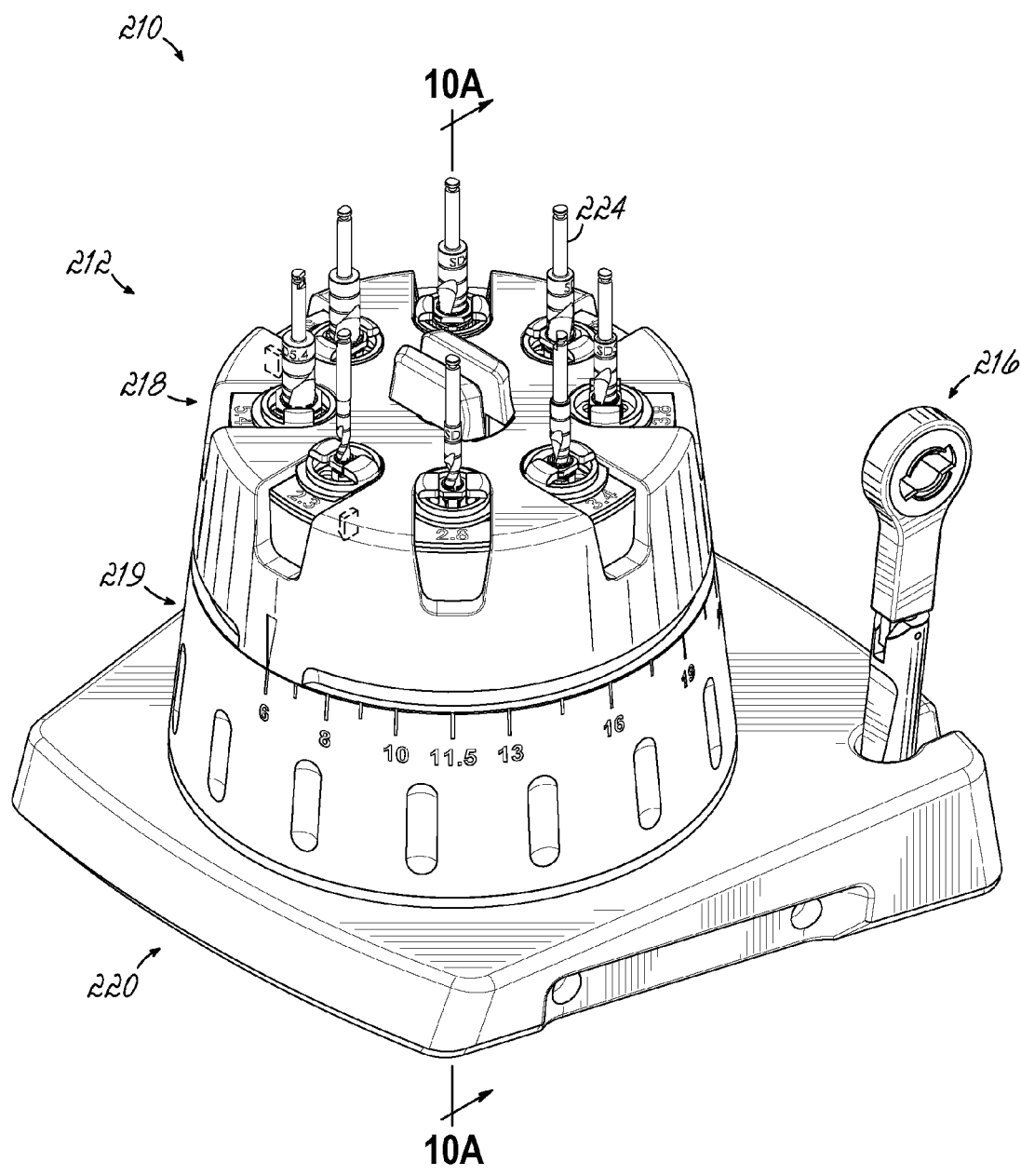
FIG. 9B is a schematic representation of an alternative embodiment of a drill limit system.
Figure 9C:
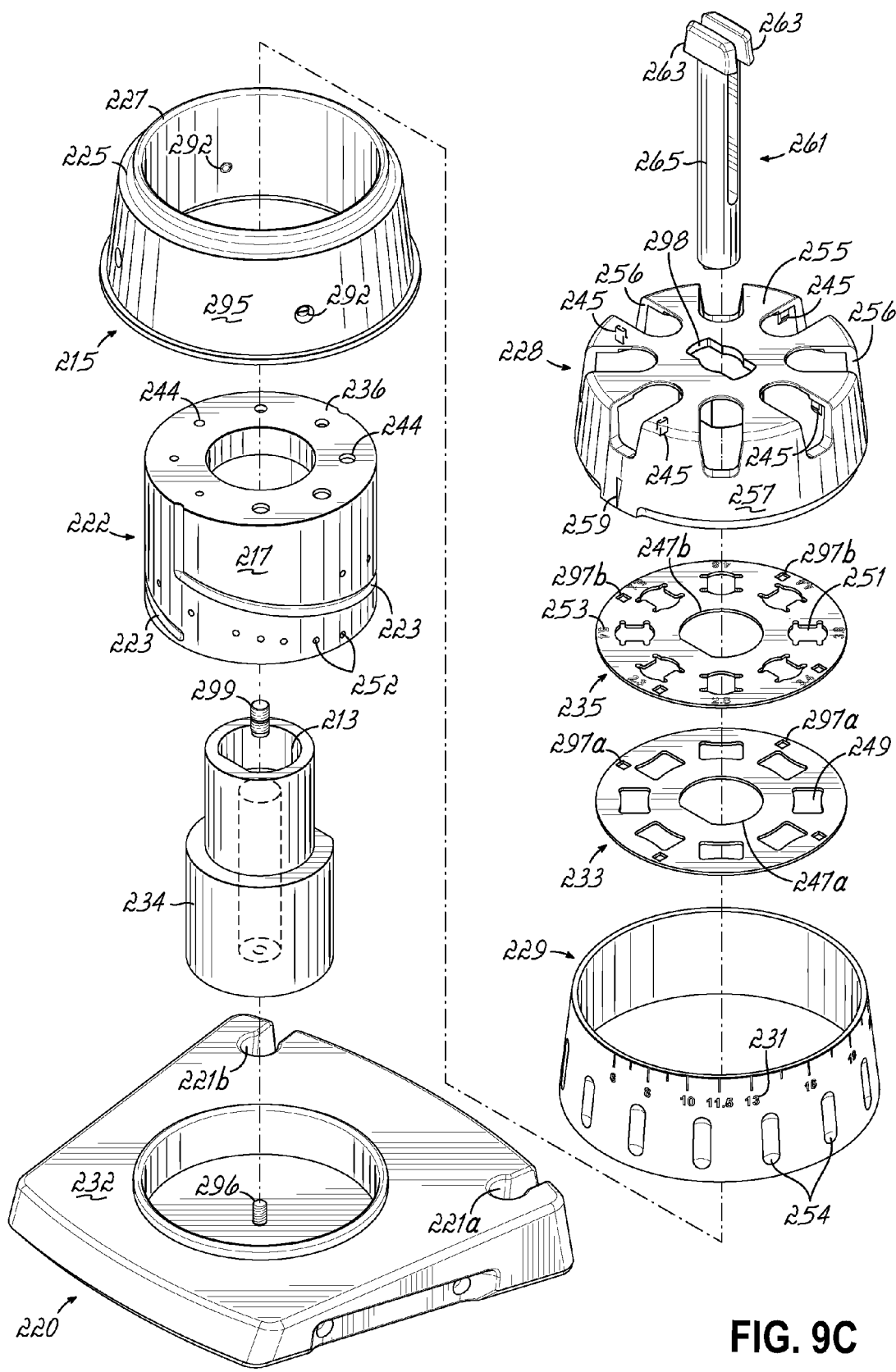
FIG. 9C is a schematic representation of the drill limit system as shown in FIG. 9B.

Cap 128 is composed of a top surface 155 and annular sidewall 157. Top surface 155 of cap 128 contains a plurality of openings 156, which generally align with flexing element alignment openings 151 of upper plate 135 and the openings 149 and guide protrusions 139 of bottom plate 133. The annular sidewall 157 of cap 128 includes indicia 159 configured to align with the appropriate indicia of depth 131 of depth control member 115 when the drill limit system is in use, the mode of which is described in further detail below. On the obverse side of top surface 155, as shown in FIG. 9A, cap 128 contains securing portion 161, which is generally cylindrical but may contain an aligning feature, such as flat surface 163 shown. To assemble the holder portion, securing portion 161 passes through the center holes 147b, 147a of upper and bottom plates 135, 133. The tabs 141 are then used to rotate the bottom plate 133 such that the guide protrusions 139 engage with ridges 126 and generally align with openings 156. The securing portion 161 can then be passed through depth control member 115 and variable depth platform 122, into a complementary bore 113 of shaft 134. Spring-loaded biased pins 165 may be used to secure the securing portion 161 of cap 128 to the shaft (see FIGS. 10 and 11).

As best shown in FIGS. 12, 12A, and 14-15, drill stop 114 is composed of nut portion 164, including internal threads and a plurality of flats 168, and grip portion 166 with a clip feature 170. Nut portion 164 and grip portion 166 both have an internal diameter slightly larger than the outer diameter of the drill bit 124. The drill bit 124 is passed through the inner diameter of the nut portion 164 and grip portion 166 within the rotatable socket drive adapter 167 and flexing element 162 of holder portion 118, with the tip 173 of drill bit 124 resting in recess 144 of the top surface 136 of variable depth platform 122. When drill stop 114 comes in contact with flexing element 162, resilient fingers 175 engage clip feature 170 of grip portion 166.

Figure 16A:
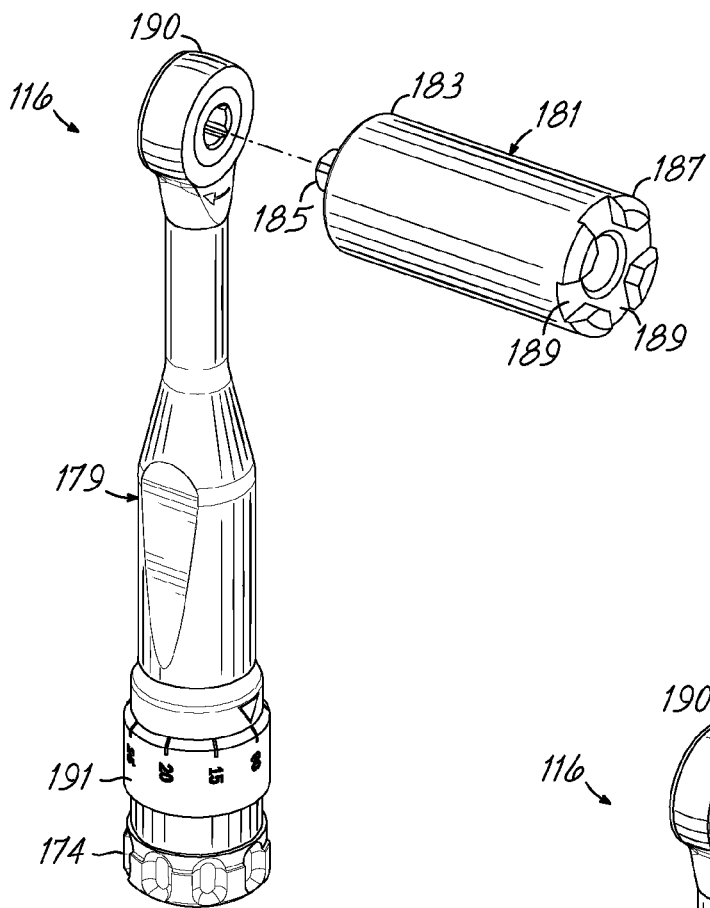
FIG. 16A is schematic view of the torque-control tool of the drill limit system shown in FIG. 8, in its disassembled state.
Figure 16B:
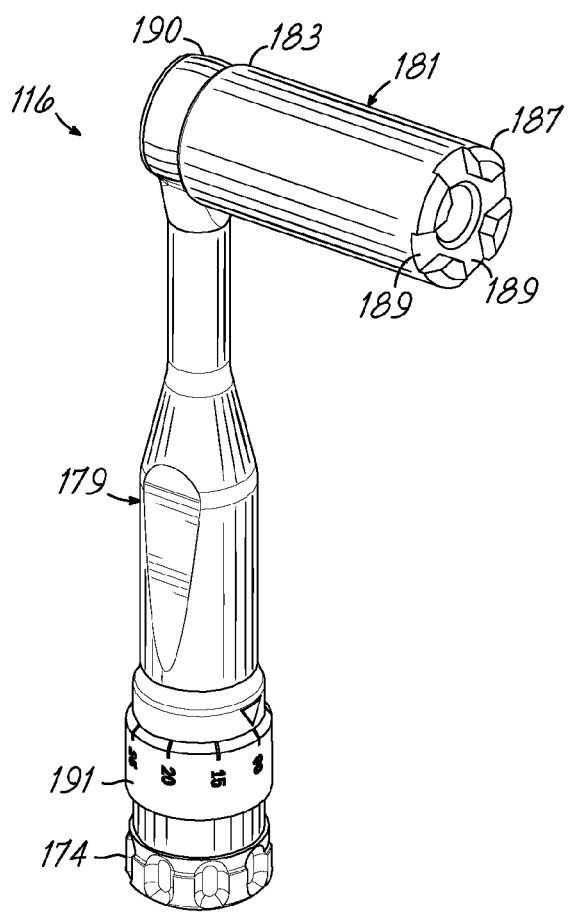
FIG. 16B is a schematic view of the torque-control tool of the drill limit system shown in FIG. 8, as assembled for use.

Torque-control tool 116, as best shown in FIGS. 16A and 16B, is composed of two parts: ratchet 179 and socket adapter 181. When not in use, the torque-control tool 116 may conveniently rest in specially adapted recesses 121a, 121b on pedestal 120. In use, socket adapter 181 is composed of connecting end 183, which includes fitment 185 configured to interact with ratchet 179, and torque end 187, which includes slots 189 configured to interact with wings 171 of rotatable socket drive adapter 167. Ratchet 179 includes a handle end 174 and a connecting end 190 configured to interact with fitment 185 of connecting end 183 of socket adapter 181. Handle end 174 includes a torque-control member 191, which can be used to set a desired torque value. Such torque limit mechanisms and ratchets are known in the art and will not be discussed in further detail.

Figure 16C:
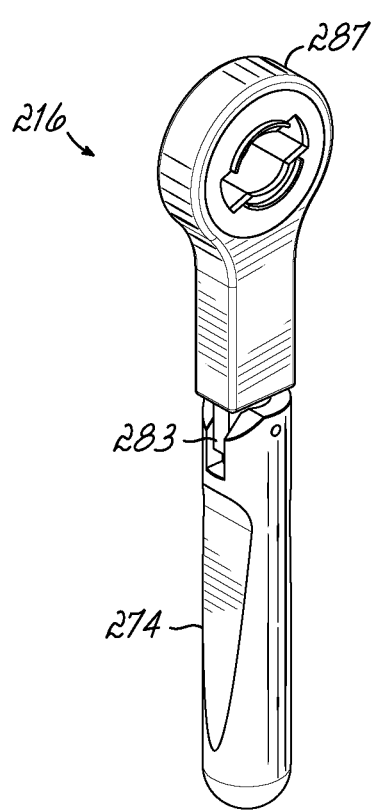
FIG. 16C is a schematic view of an alternative embodiment of the torque-control tool.
Figure 16D:
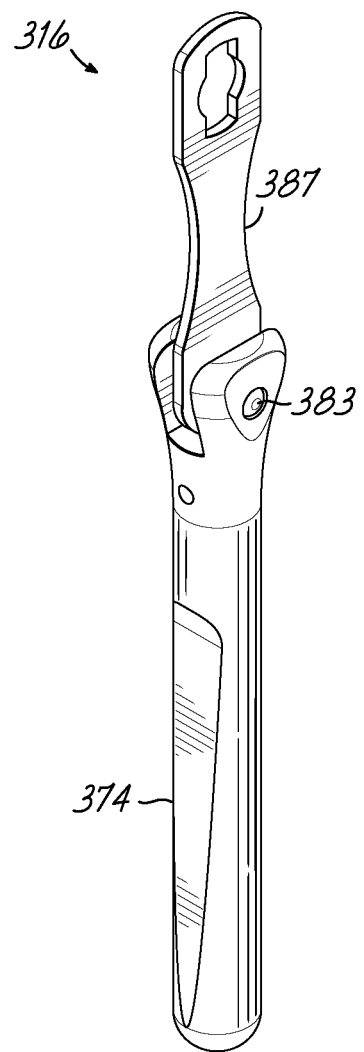
FIG. 16D is a schematic view of an alternative embodiment of the torque-control tool.

Alternatively, torque-control tool 216 is shown in FIG. 16C, and torque-control tool 316 is shown in FIG. 16D. Both include a handle portion 274, 374, and a torque end 287, 387. The torque ends 287, 387 are attached to handle portion 274, 374, through hinge portion 283, 383, which allows the handle portion 274, 374, to swivel relative to the torque end 287, 387. This ability to swivel may, for example, allow the practitioner better grip and control on the torque-control tool 216, 316. Also, the hinge portion 283, 383 may include a torque limit mechanism. Each of the disclosed embodiments of the drill limit system 110, 210 may use any of the torque-control tools 116, 216, 316, in principle.

FIGS. 9B, 9C, 10A, 13, 13A, and 13B, show an alternative embodiment of the drill limit system 210, where like labels indicate similar components. The drill limit system 210 includes a drill platform 212 and a torque-control tool 216. The drill platform 212 includes holder portion 218, depth control portion 219, and pedestal 220.

Pedestal 220 is composed of base 232 and shaft 234. Base 232 contains specially adapted recesses 221a and 221b and is generally planar and configured for resting on a relatively flat surface, such as a table, countertop, tray, etc. during the medical procedure for easy access by the practitioner. Shaft 234 is generally cylindrical, projecting away from the base 232, and is configured for slidably receiving the depth control portion 219 such that the depth control portion 219 is generally free to move in a certain direction on the shaft 234, which is shown as a vertical direction in the figures. The shaft 234 is held to pedestal 220 via bolt 296.

Depth control portion 219 is composed of variable depth platform 222, which fits over shaft 234, depth control member 215, and indicator ring 229. Variable depth platform 222 is composed of top surface 236, having a plurality of recesses 244 configured to receive the tip 273 of drill bits 224, and an annular sidewall 217, which contains helical groove 223 and depth notches 252. Depth control member 215, which is configured to interact with variable depth platform 222 in the same manner as discussed above for depth control member 115, (i.e., an interaction between glide elements 292 and the helical groove 223), is composed of a top surface 225 with a raised joining ring member 227 and an annular sidewall 295. Raised joining ring member 227 is configured to interact with cap 228 of the holder portion 218. The indicator ring 229 fits over the depth control member 215 and contains a plurality of grip features 254 to aid the practitioner in turning the depth control member 215, as well as a plurality of indicia of depth 231.

Holder portion 218 is composed of bottom plate 233, upper plate 235, flexing element 262, rotatable socket drive adapter 267, and cap 228. The drill bits 224 and drill stops 214 rest within holder portion 218 when not in use during the medical procedure. Bottom plate 233 and upper plate 235 possess an annular geometry of substantially equal diameter. Bottom plate 233 has a center hole 247a and a plurality of openings 249 at least as large as the diameter of the drill bit 224. Upper plate 235 also includes center hole 247b. The cap 228, upper plate 235, and bottom plate 233, are held in contact via tabs 245 of cap 228 and openings 297a, 297b. Flexing element 262 is configured to fit within a plurality of flexing element alignment openings 251 of upper plate 235, which generally align with openings 249 of the bottom plate 233. The number of bottom plate openings 249 and upper plate flexing element alignment openings 251 is determined by the number of drill bits 224 and drill stops 214 desired. In the figures, eight drill bits 224 and drill stops 214 are shown, but the invention is not so limited. Although drill limit systems 110 and 210 share many similarities, as best shown in FIGS. 13-13B, a difference between the two drill limit systems, is that in flexing element 262, C-spring 275, as opposed to resilient fingers 175, is used to removably connect grip portion 266 to holder portion 218, through ring grooves 270. In this manner, the drill bit 224 and drill stop 214 can be removed from and replaced on flexing element 262 with ease. Rotatable socket drive adapter 267 functions in a similar manner to rotatable socket drive adapter 167. As discussed above, torque-control tools 116, 216, and 316, are interchangeable within the various disclosed embodiments.

Conveniently, one or both of the flexing element 262 and the rotatable socket drive adapter 267 may be color coded to quickly indicate to the practitioner the matching sets of components. Additionally, a plurality of indicia 253 may be printed, etched, or otherwise included, proximate to the flexing element alignment openings 251 of upper plate 235 to indicate to the practitioner the diameter of the drill bit 224 housed at each flexing element alignment opening 251.

Cap 228 is composed of a top surface 255 and annular sidewall 257. Top surface 255 of cap 228 contains a plurality of holes 256, which generally align with flexing element alignment openings 251 of upper plate 235 and the openings 249 of bottom plate 233. Top surface 255 of cap 228 also includes opening 298. The annular sidewall 257 of cap 228 includes indicia 259 configured to align with the appropriate indicia of depth 231 of indicator ring 229 when the drill limit system is in use, the mode of which is similar to that of drill limit system 110 described above. When attaching the holder portion 218 to the depth control portion 219 and the pedestal 220, the shaft 265 of joining member 261 is passed through depth control portion 219 and affixed to shaft 234 with threaded bolt receiver 299. Threaded bolt receiver 299 includes an inner threaded surface and an outer threaded surface. The inner threaded surface attaches to bolt 296. Shaft 265, in turn, includes threading complementary to the outer threaded surface of threaded bolt receiver 299. Once the joining member 261 is affixed to the shaft 234, the bottom plate 133, upper plate 135, and cap 228, are affixed to joining member 261 and held in place by clips 263 and opening 298. Thus, removing the holder portion 218 from the drill limit system 210 is easily accomplished by pinching together clips 263 and lifting the holder portion 218 away from the depth control portion 219.

Turning now to the operation of drill limit system 110, the practitioner places the drill stop 114 in the appropriate location of the holder portion 118 and then passes drill bit 124 through drill stop 114. The drill bit 124 is freely moveable in the same direction as the variable depth platform 122, which is shown as the vertical direction in the figures, until the nut portion 164 is rotated to clamp the grip portion 166 onto the drill bit 124. Because drill bit 124 is freely moveable, the tip 173 of the drill bit 124 rests in recess 144 of the top surface 136 of variable depth platform 122 at a uniform vertical position relative to the holder portion 118. In this respect, each recess 144 generally vertically aligns with a respective drill stop 114, such that each drill bit 124 is held within the holder portion 118 in a generally vertical orientation.

Figure 10:
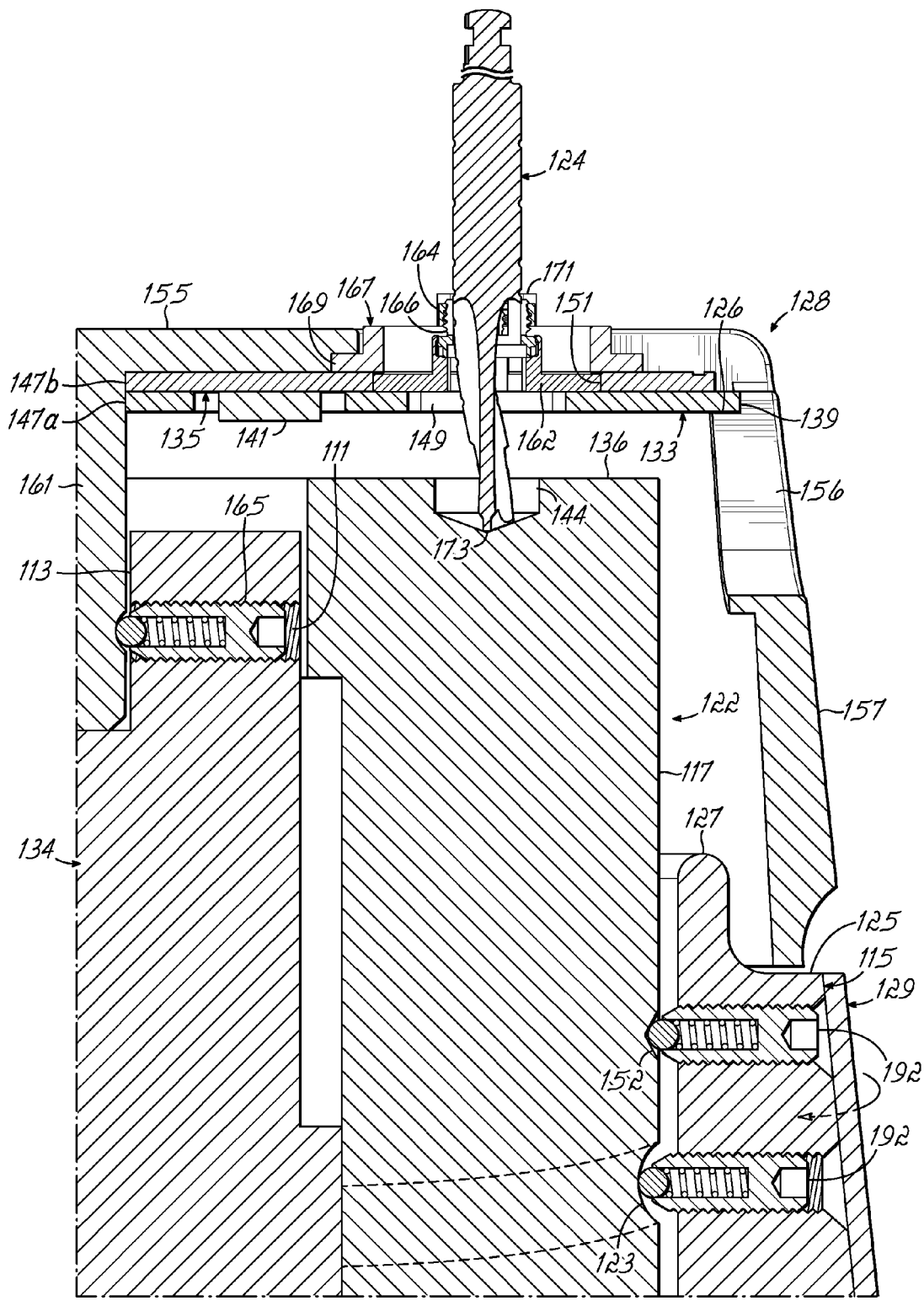
FIG. 10 is a schematic cross-sectional view of the drill limit system shown in FIG. 8 taken generally along line 10-10.
Figure 10A:
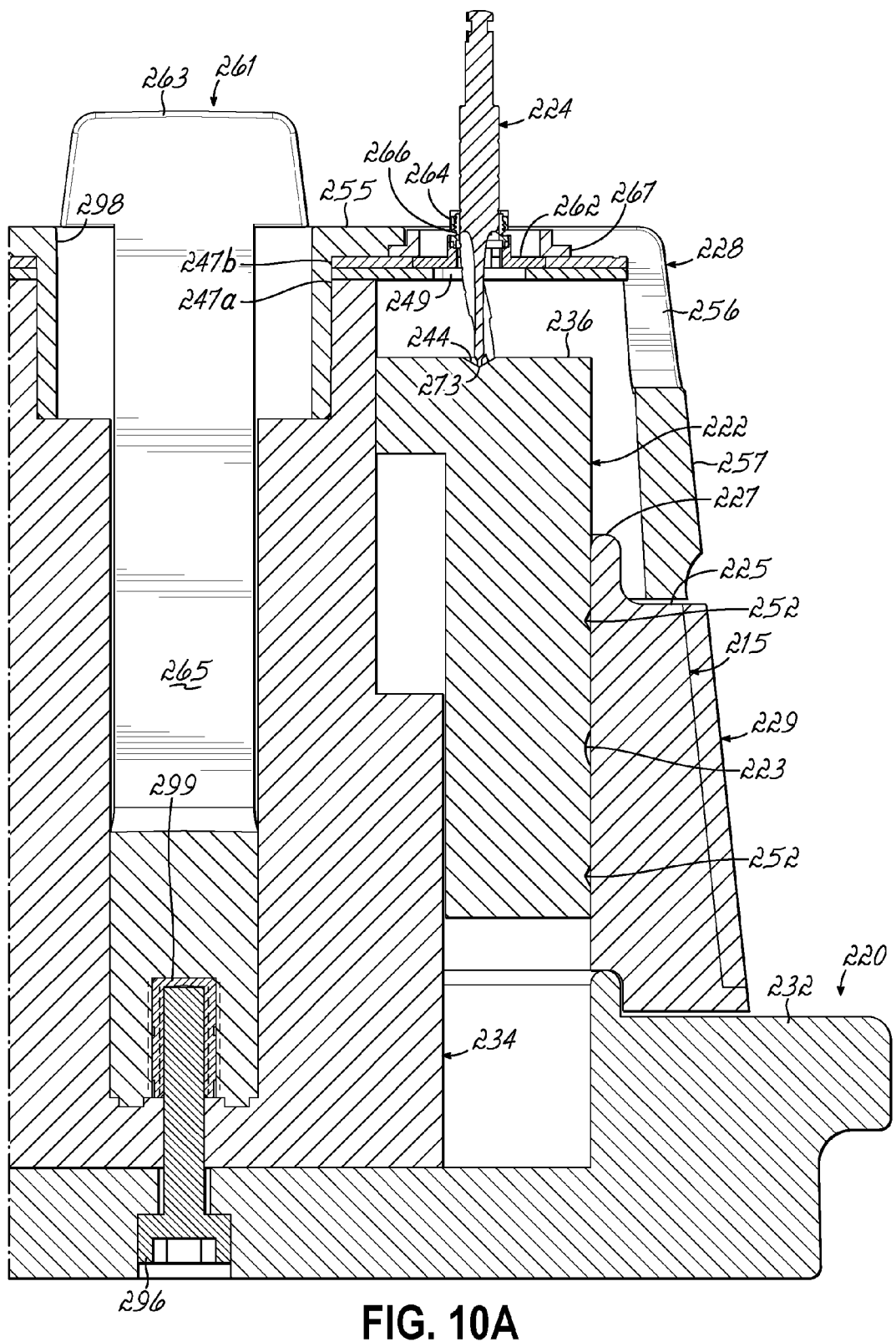
FIG. 10A is a schematic cross-sectional view of the drill limit system shown in FIG. 9B.
Figure 11:
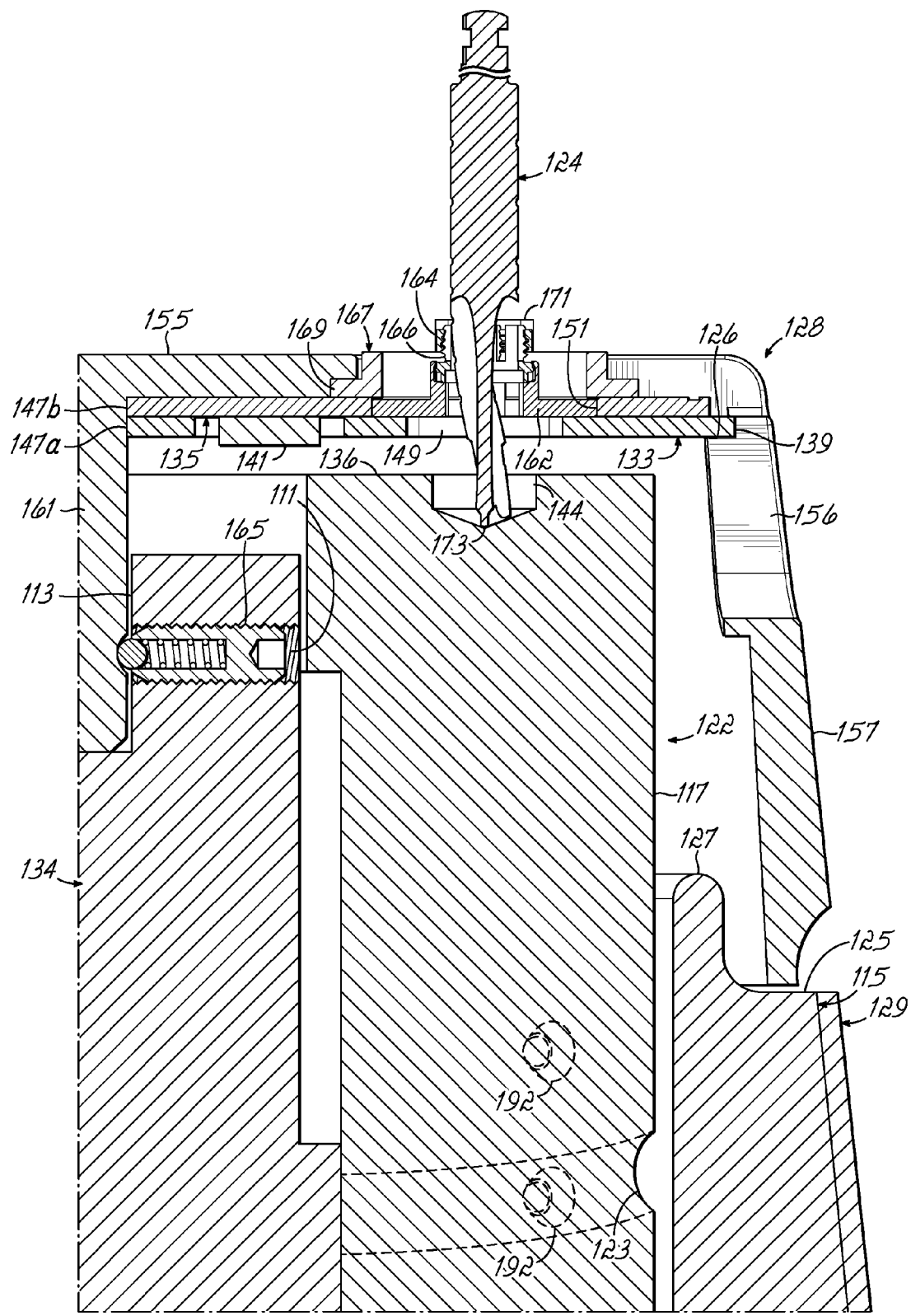
FIG. 11 is a schematic cross-sectional view of the drill limit system shown in FIG. 8 taken generally along line 10-10, in which the depth control platform 122 has been raised relative to FIG. 10.
Figures 12, 12A:
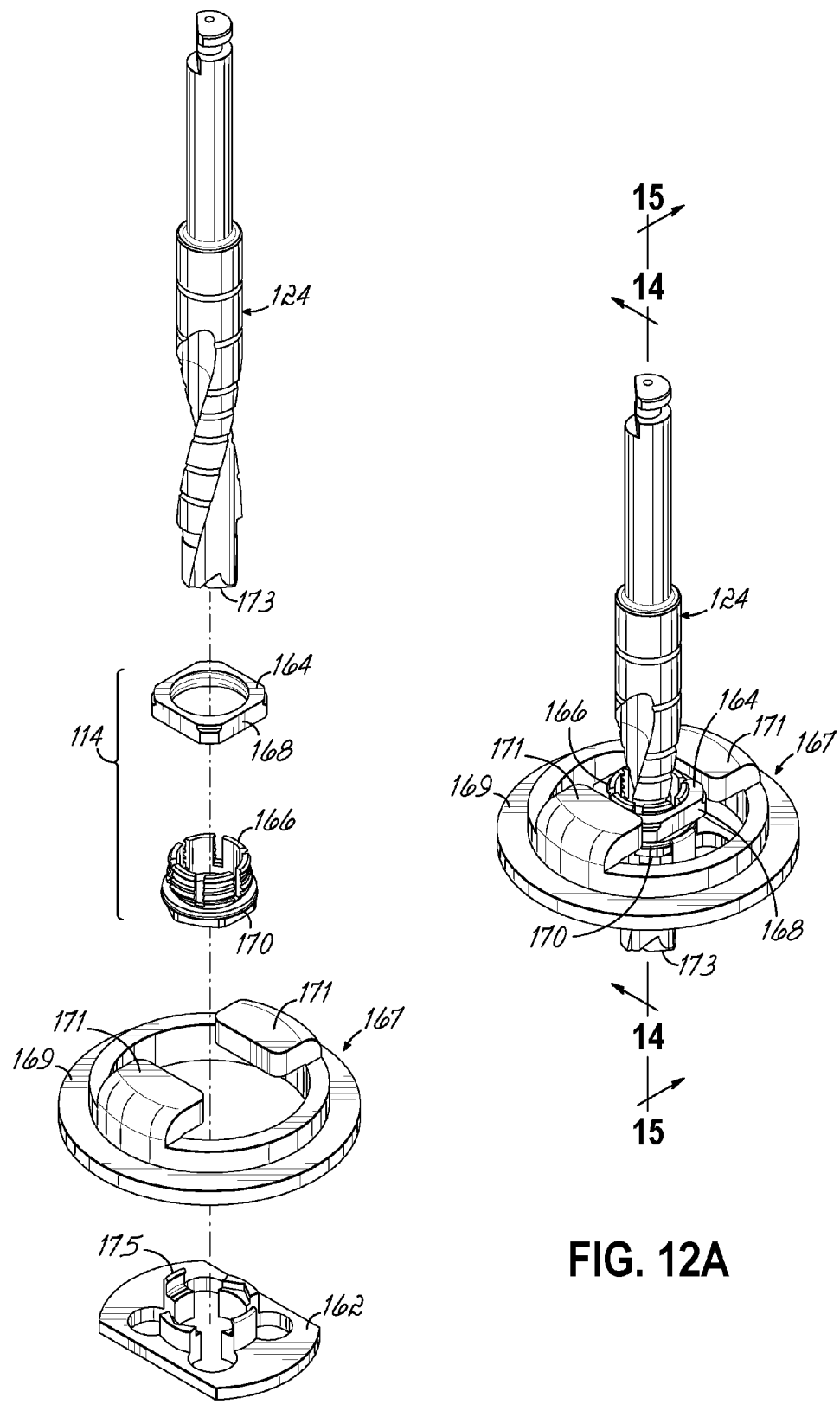
FIG. 12 is a schematic view of the drill bit assembly.
FIG. 12A is a front perspective view of the drill bit assembly shown in FIG. 12 in its assembled state.
Figure 14:
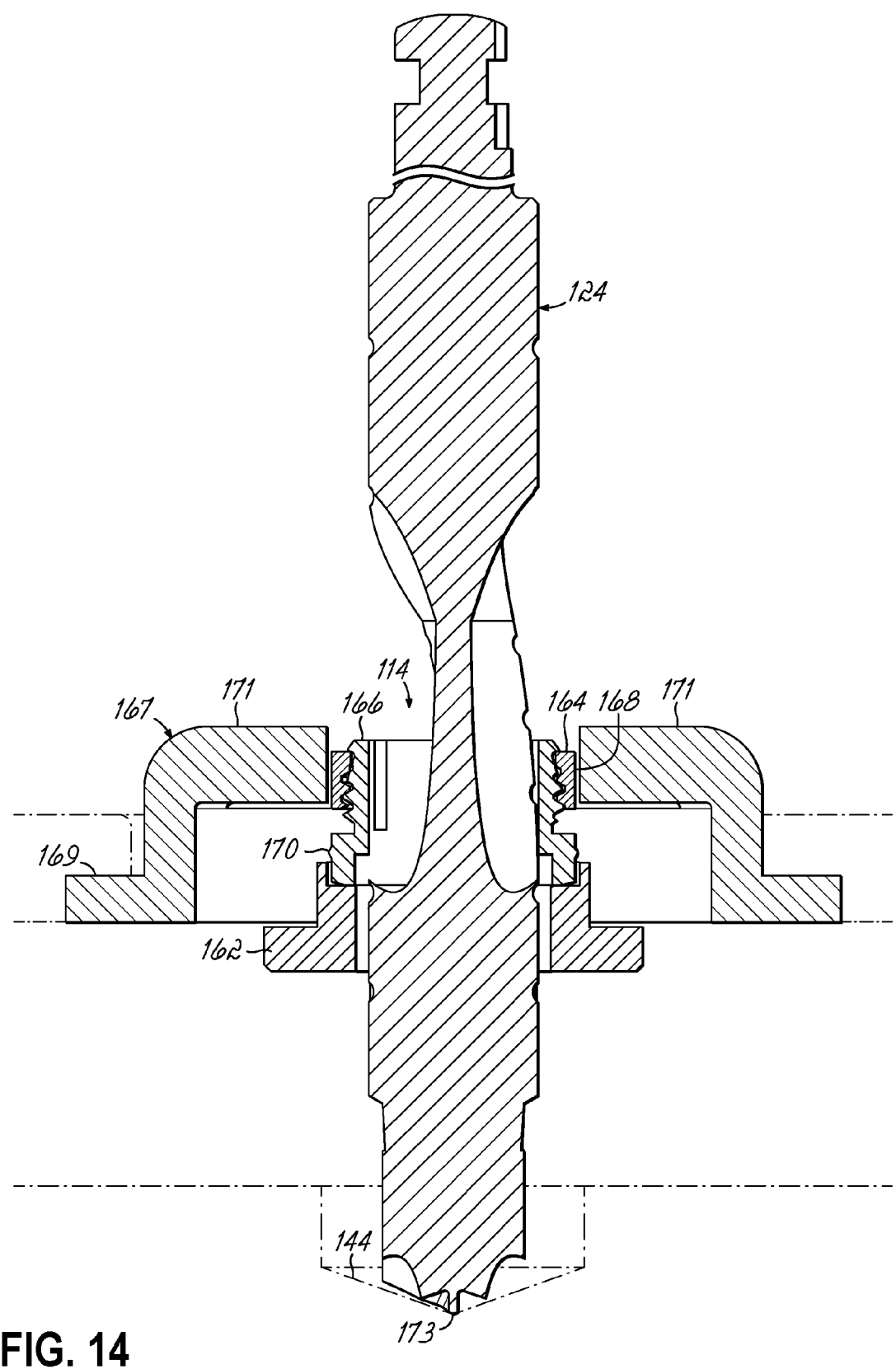
FIG. 14 is a schematic cross-sectional view of the drill bit assembly shown in FIG. 12A taken generally along the 14-14 line.
Figure 15:
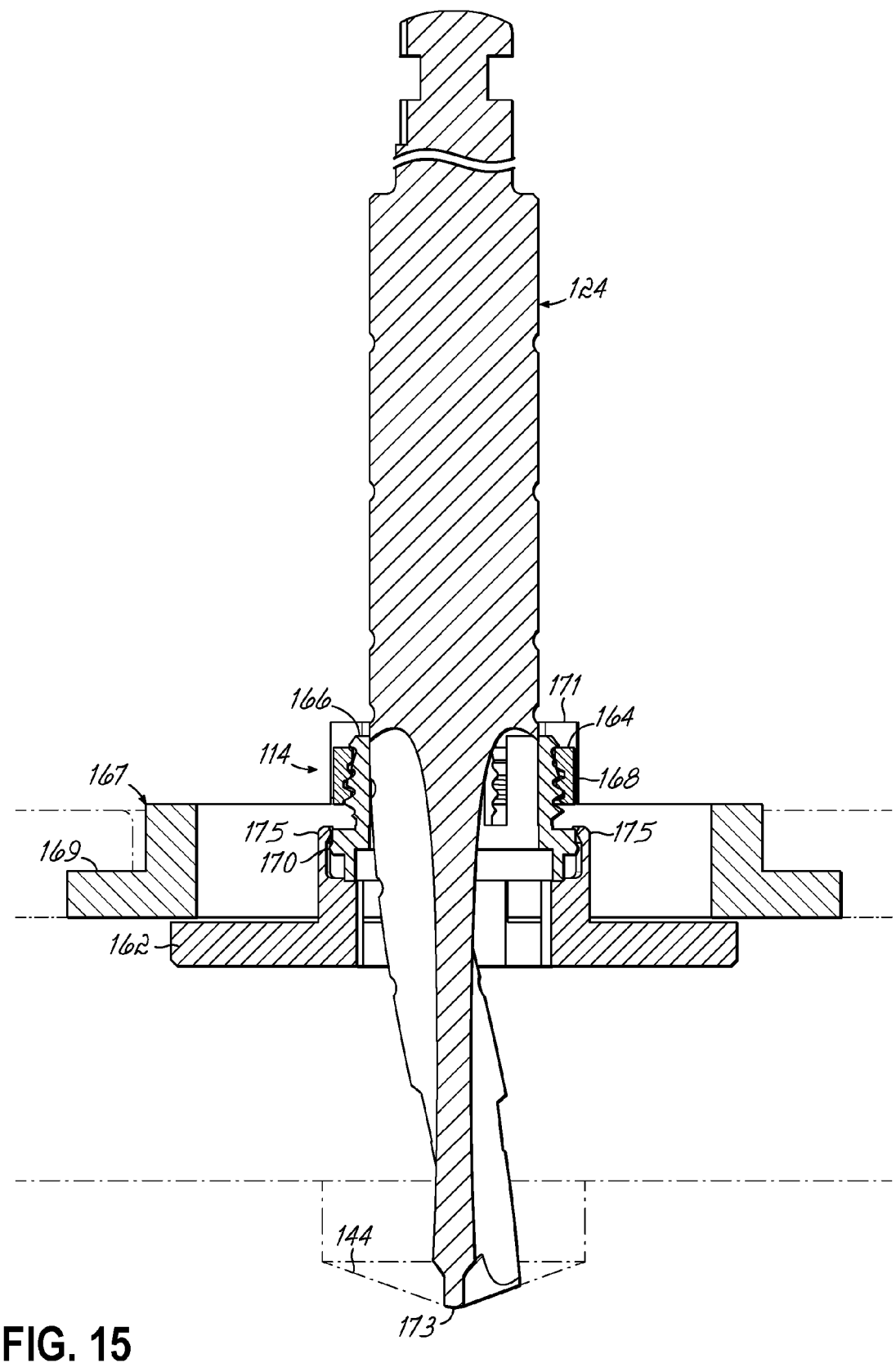
FIG. 15 is a schematic cross-sectional view of the drill bit assembly shown in FIG. 12A taken generally along the 15-15 line.

To set the height of the drill stop 114, the practitioner rotates the indicator ring 129 to the desired height as indicated by aligning indicia 159 of annular sidewall 157 of cap 128 with the appropriate indicia of depth 131 of indicator ring 129. The rotation of indicator ring 129 rotates depth control member 115. As best shown in FIGS. 10 and 11, glide element 192 on the inside surface 193 of annular sidewall 195 of depth control member 115 rides along helical groove 123 as the depth control member 115 is rotated to the desired height setting. The glide element 192 may be, for example, a biased pin or a ball bearing. Depth notches 152, which interact with one of the glide elements 192 on the inside surface 193 of annular sidewall 195 of depth control member 115, provide a tactile and audible indication that the height indicated by the appropriate indicia of depth 131 has been reached. However, the practitioner may rotate the depth control member 115 to be slightly more or slightly less than the indicated height to allow fine control of the height of drill stop 114. As the depth control member 115 is rotated, the motion of the glide element 192 in helical groove 123 raises or lowers the variable depth platform 122, which in turn raises or lowers the drill bit 124. As opposed to drill limit system 10, in drill limit system 110, the variable depth platform 122 moves relative to the base 132 while the holder portion 118 is stationary relative to the base 132. As described above, drill bit 124 is freely moveable in the same direction as the variable depth platform 122.

Figure 17:
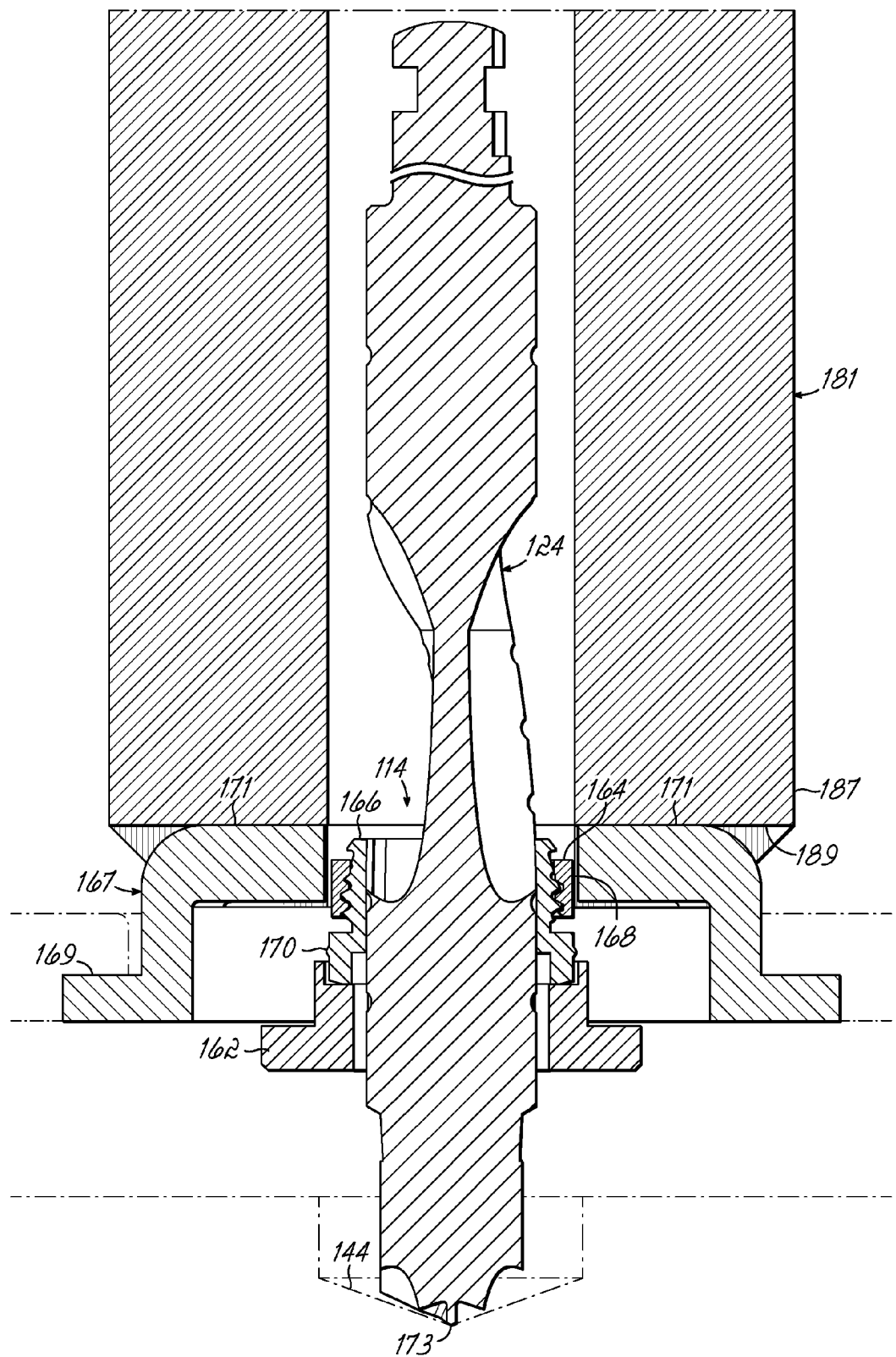
FIG. 17 is a schematic cross-sectional view of the drill bit assembly shown in FIG. 12A taken generally along the 14-14 line with the socket adapter of the torque-control tool shown in FIG. 16B engaged.
Figure 18:
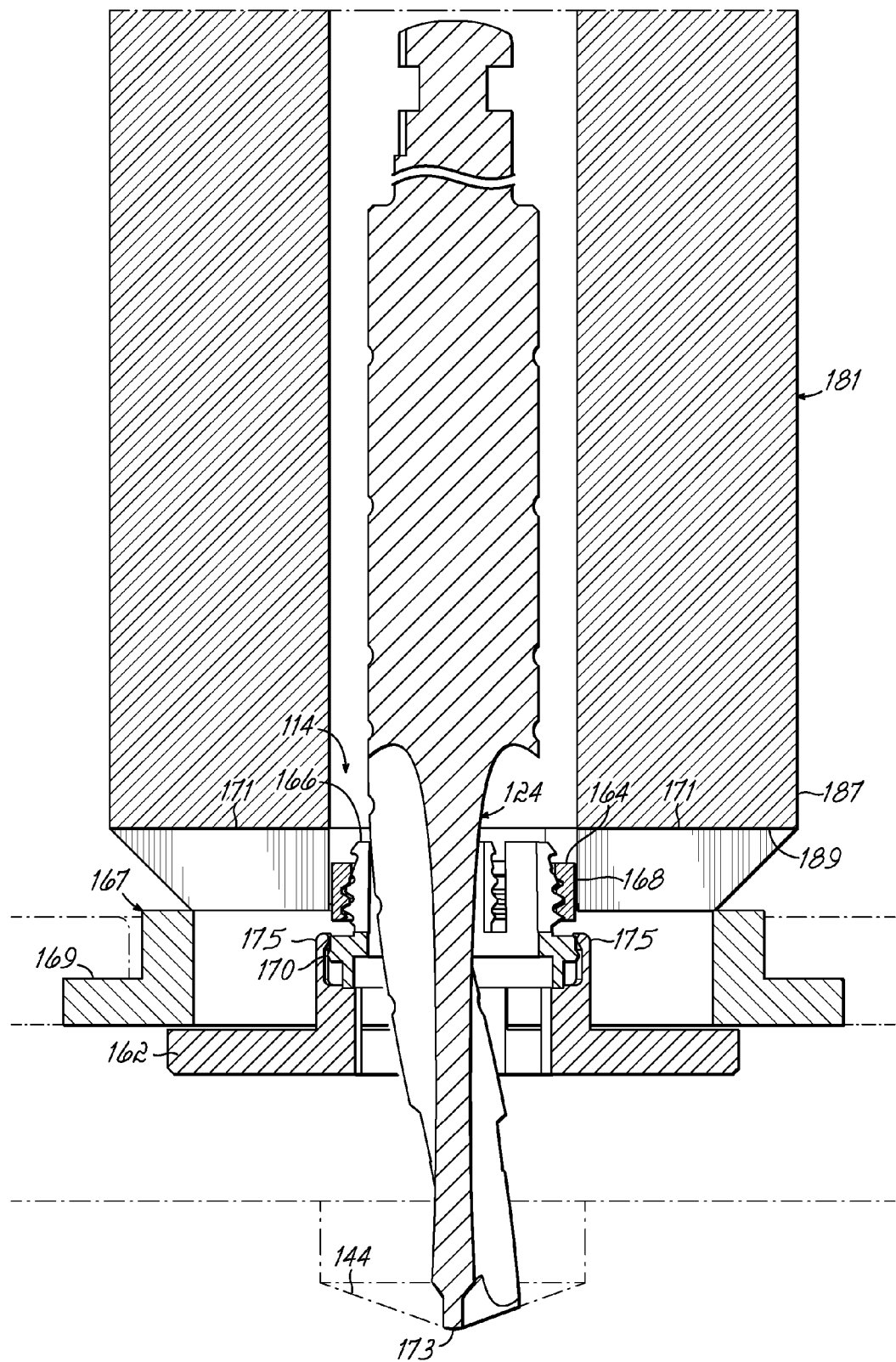
FIG. 18 is a schematic cross-sectional view of the drill bit assembly shown in FIG. 12A taken generally along the 15-15 line with the socket adapter of the torque-control tool shown in FIG. 16B engaged.

Once the desired height has been set, torque-control tool 116, assembled as described above, is used to turn rotatable socket drive adapter 167. As rotatable socket drive adapter 167 is turned, due to its contact with flats 168 of nut portion 164, the movement causes turning of nut portion 164 with the grip portion 166 remaining stationary due to its interaction with flexing element 162. In this manner, nut portion 164, and more particularly the resilient split fingers thereof, can tighten and loosen grip portion 166 on drill bit 124, as best shown in FIGS. 17 and 18. Tightening occurs until a preselected torque value, as set using torque-control member 191, is reached, at which point connecting end 190 of ratchet 179 ratchets free and will no longer tighten the nut portion 164. This process is repeated for each of the drill stops 114 and corresponding drill bits 124 in the drill platform 112.

Once the grip portion 166 is tightened to drill bit 124, the drill bit 124 is ready for use. As described above, drill bit 124 with drill stop 114 is placed within flexing element 162 and held in a generally vertical orientation via resilient fingers 175, which engage clip feature 170 of grip portion 166. The practitioner removes the drill bits 124 from the smallest diameter drill bit to the largest diameter drill bit necessary to drill a desired hole in the bone. Drill bit 124 may coupled to a dental drill (not shown) and disengaged from the holder portion 118, by overcoming the force of the interaction between the resilient fingers 175 and clip feature 170. In this manner, the practitioner never needs to touch the drill bits 124 during the procedure. The hole in the bone is drilled with the drill bit 124 to the desirable depth as indicated by the drill stop 114. After the depth of the hole is such that the edge of the drill stop is reached, the practitioner removes the drill from the hole and replaces the drill bit 124 into its corresponding opening 156 until the resilient fingers 175 reengage the clip feature 170 of grip portion 166 to secure the drill bit 24 to the holder portion 118. The practitioner repeats this disengaging, drilling, and replacing of the drill bits 124 with drill stops 114 until the hole in the bone is the desired diameter.

Once the hole in the bone is complete, the practitioner loosens each of the drill stops 114 from the drill bits 124 using the torque-control tool as discussed above, and removes the drill bits 124 from the drill platform 112. The drill limit system 110 can then be disassembled for cleaning and other routine maintenance in order to prepare the drill limit system 110 for another medical procedure.

In principle, drill limit system 210 operates similarly to drill limit system 110. The height of the drill bits 224 is set simultaneously by setting the depth control portion 219 to the desired height. Then the drill stop 214 is engaged with drill bit 224 by rotating rotatable socket drive adapter 267, which in turn rotates nut portion 264, ultimately causing grip portion 266 to grip the drill bit 224. The drill bits 224 are then removed from the holder portion 218 by disengaging ring grooves 270 of grip portion 266 of drill stop 214 from the flexing element 262, working from the smallest diameter drill bit to the largest desired diameter drill bit. In this manner, a hole may be drilled in a bone to a desired depth without overheating the bone.

While the present invention has been illustrated by the description of one or more embodiments thereof, and while the embodiments have been described in considerable detail, they are not intended to restrict or in any way limit the scope of the appended claims to such detail. For example, the drill limit system has been described above with respect for use with a tooth and/or jawbone. However it will be appreciated that the drill limit system may be used in any variety of medical procedures, such as an endodontic procedure. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be from such details without departing from the scope of the general inventive concept.

What is claimed is:

1. A drill limit system for providing a plurality of drill stops with drill bits, comprising:
a holder including a plurality of drill stops removably coupled to the holder and configured to receive a drill bit therethrough, wherein the drill stops have a first state in which the drill bits are configured to be movable relative to the drill stops and a second state in which the drill stops are configured to be fixedly secured to the drill bits; and
a platform operatively coupled to the holder and having a surface configured to engage a tip end of the drill bits, wherein the holder and the platform are movable relative to each other such that the position of the drill stop relative to the drill bit may be selectively varied in order to locate the drill stop at a desired position on the drill bit.

2. The drill limit system of claim 1, wherein the platform is configured to be stationary and the holder is configured to be movable relative to the platform.

3. The drill limit system of claim 1, wherein the holder is configured to be stationary and the platform is configured to be movable relative to the holder.

4. The drill limit system of claim 3, further comprising a rotatable adjustment member, wherein rotation of the adjustment member causes movement of the platform relative to the holder.

5. The drill limit system of claim 4, wherein the platform includes a helical groove and the adjustment member includes a glide element configured to engage the helical groove, wherein rotation of the adjustment member causes the glide element to move along the helical groove to move the platform relative to the holder.

6. The drill limit system of claim 1, wherein the holder includes one or more spring clips for selectively engaging the drill stops to and releasing the drill stops from the holder.

7. The drill limit system of claim 6, wherein the spring clips include one or more spring fingers.

8. The drill limit system of claim 6, wherein the spring clips include C-springs.

9. The drill limit system of claim 6, wherein the drill stops include a clip feature configured to cooperate with the spring clips for selectively engaging the drill stops to and releasing the drill stops from the holder.

10. The drill limit system of claim 1, wherein the drill stops comprise:
a nut portion; and
a grip portion threadably coupled to the nut portion, wherein rotation of the nut portion relative to the grip portion transitions the drill stops between the first and second states.

11. The drill limit system of claim 10, wherein the grip portion includes a clip feature configured to cooperate with one or more spring clips on the holder for selectively engaging to and releasing from the holder.

12. The drill limit system of claim 1, further comprising indicia for indicating the position of the drill stop on the drill bit.

13. The drill limit system of claim 1, wherein the drill limit system includes color coding of the plurality of drill bits.

14. The drill limit system of claim 1, wherein the drill stops comprise a nut portion and a grip portion threadably coupled to the nut portion, rotation of the nut portion relative to the grip portion transitions the drill stops between the first and second states, and the holder includes a rotatable member configured to rotate the nut portion relative to the grip portion.

15. The drill limit system of claim 1, further comprising a torque-control tool configured to cooperate with the drill stops to transition the drill stops between the first and second states.

16. A method for attaching drill stops to a drill bit, comprising:
providing a holder and a platform movable relative to each other, the holder including a plurality of drill stops removably coupled thereto;
inserting a plurality of drill bits through respective drill stops in the holder so that a portion of the drill bits engage the platform;
moving the holder and platform relative to each other to select a desired height of the drill stops on each of the drill bits; and
engaging a drill stop onto each of the plurality of drill bits at the selected height.

17. The method of claim 16, further comprising:
moving the holder relative to the platform or the platform relative to the holder to set the height.

18. The method of claim 16, further comprising:
rotating a first portion of the drill stop relative to a second portion of the drill stop to engage the drill stop onto each of the plurality of drill bits.

19. The method of claim 18, further comprising:
rotating the first portion of the drill stop relative to the second portion of the drill stop by rotating a rotatable member of the holder that is in contact with the first portion of the drill stop.

20. The method of claim 16, further comprising:
providing the drill stops to the holder before providing the plurality of drill bits.

* * * * *